(12) United States Patent
Chakkumkal et al.

(10) Patent No.: US 10,500,283 B2
(45) Date of Patent: Dec. 10, 2019

(54) VACCINE COMPOSITION CAPABLE OF INDUCING MEMORY ANTIBODY RESPONSE FROM SINGLE POINT IMMUNIZATION

(75) Inventors: Anish Chakkumkal, New Delhi (IN); Amulya Kumar Panda, New Delhi (IN)

(73) Assignee: National Institute of Immunology, New Delhi (IN)

( * ) Notice: Subject to any disclaimer, the term of this patent is extended or adjusted under 35 U.S.C. 154(b) by 99 days.

(21) Appl. No.: 14/122,923

(22) PCT Filed: May 29, 2012

(86) PCT No.: PCT/IB2012/052664
§ 371 (c)(1),
(2), (4) Date: May 7, 2014

(87) PCT Pub. No.: WO2012/164480
PCT Pub. Date: Dec. 6, 2012

(65) Prior Publication Data
US 2014/0242117 A1    Aug. 28, 2014

(30) Foreign Application Priority Data

May 30, 2011   (IN) .......................... 1539/DEL/2011

(51) Int. Cl.
| | | |
|---|---|---|
| *A61K 39/112* | (2006.01) | |
| *A61K 9/00* | (2006.01) | |
| *A01N 25/26* | (2006.01) | |
| *A01N 25/28* | (2006.01) | |
| *A61K 39/00* | (2006.01) | |
| *A61K 39/38* | (2006.01) | |
| *A61K 47/34* | (2017.01) | |

(52) U.S. Cl.
CPC .......... *A61K 47/34* (2013.01); *A61K 39/0275* (2013.01); *A61K 2039/545* (2013.01); *A61K 2039/55544* (2013.01); *A61K 2039/55555* (2013.01); *A61K 2039/6093* (2013.01); *Y02A 50/484* (2018.01)

(58) Field of Classification Search
CPC .... A61K 39/0275; A61K 47/10; A61K 38/00; A01N 25/26
See application file for complete search history.

(56) References Cited

U.S. PATENT DOCUMENTS

| | | | | |
|---|---|---|---|---|
| 5,407,609 | A * | 4/1995 | Tice ..................... | A61K 9/1694 264/4.1 |
| 5,417,986 | A * | 5/1995 | Reid .................. | A61K 39/0258 424/422 |
| 2004/0057958 | A1* | 3/2004 | Waggoner, Jr. ...... | A61K 39/015 424/184.1 |
| 2004/0213806 | A1* | 10/2004 | Demil ................ | A61K 39/0275 424/202.1 |
| 2007/0258889 | A1* | 11/2007 | Douglas ............... | A61K 9/5184 424/1.37 |
| 2011/0038900 | A1* | 2/2011 | Chakrapani .......... | A61K 39/095 424/400 |
| 2012/0231086 | A1* | 9/2012 | Killen .................. | A61K 39/025 424/499 |
| 2014/0086989 | A1* | 3/2014 | Killeen .............. | A61K 39/0275 424/484 |
| 2014/0154286 | A1* | 6/2014 | Malley .................. | C07K 14/31 424/190.1 |

FOREIGN PATENT DOCUMENTS

WO     0056362 A2     9/2000

OTHER PUBLICATIONS

V.D. Thiem et al. "The Vi Conjugate Typhoid Vaccine is Safe, Elecits Protective Levels of IgG Anti-Vi, and is Compatible with Routine Infant Vaccines" Clinical and Vaccine Immunology, vol. 18, No. 5, May 1, 2011, pp. 730-735 (XP55035919).
Kanchan V et al. "Memory Antibody Response From Antigen Loaded Polymer Particles and the Effect of Antigen Release Kinetics" Biomaterials, Elsevier Science Publishers, vol. 30, No. 27, Sep. 1, 2009, pp. 4763-4776 (XP026854960).
Hatzifoti Caterina et al. "Liposomal Co-entrapment of CD40mAb Induces Enhanced IgG Responses Against Bacterial Polysaccharide and Protein" Plos One, Public Library of Science, vol. 3, No. 6, Jun. 4, 2008, pp. e2368-1 (XP002566632).
Rena D. Astronomo et al. "Carbohydrate Vaccines: Developing Sweet Solutions to Sticky Situations?" Nature Reviews Drug Discovery, vol. 9, No. 4, Apr. 1, 2010, pp. 308-324 (XP55035843).
Chakkumkal Anish et al. "The Immunogenic Characteristics Associated with Multivalent Display of Vi Polysaccharide Antigen Using Biodegradable Polymer Particles" Biomaterials, vol. 33, No. 28, Oct. 1, 2012, pp. 6843-6857 (XP55035834).

* cited by examiner

*Primary Examiner* — Gary B Nickol
*Assistant Examiner* — Lakia J Jackson-Tongue
(74) *Attorney, Agent, or Firm* — Ladas & Parry LLP

(57) ABSTRACT

The present investigation relates to entrapment of carbohydrate antigen such as Vi polysaccharide of *Salmonella typhi* in poly (DL) lactide (PDLLA) and polylactide-co-glycolide (PLGA) polymer particles. The formulated product not only elicits primary antibody titers from single dose application but also evokes memory antibody titer against the T independent antigen.

8 Claims, 14 Drawing Sheets

VACCINE COMPOSITION CAPABLE OF INDUCING MEMORY ANTIBODY RESPONSE FROM SINGLE POINT IMMUNIZATION

The following specification describes the nature of the invention and particularly the manner in which it is to be performed.

FIELD OF THE INVENTION

Figure 5:
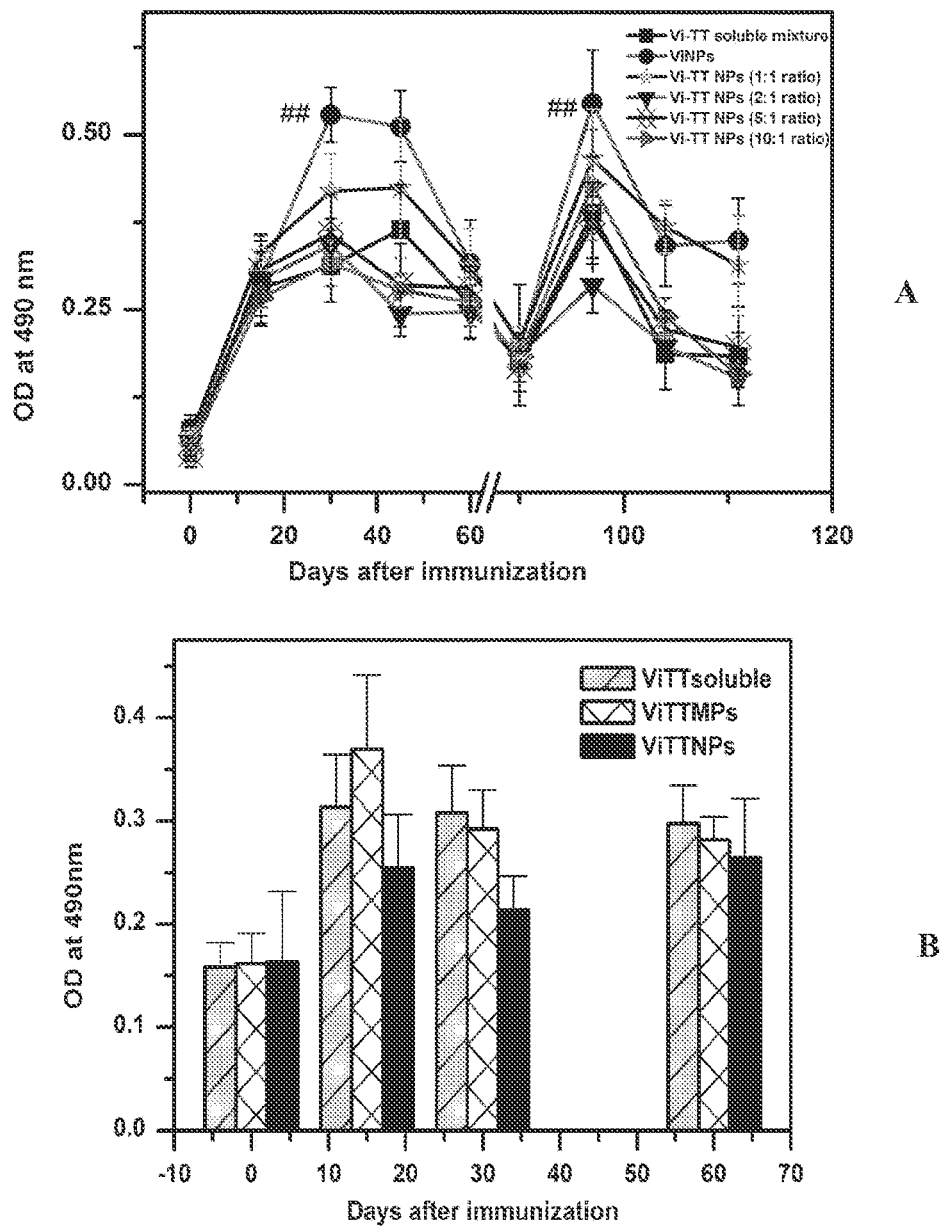

The present investigation relates to a novel typhoid vaccine to elicit the memory antibody response from a single dose immunization, produced by entrapping carbohydrate antigen such as Vi polysaccharide of *Salmonella typhi* in poly (DL) lactide (PDLLA) and polylactide-co-glycolide (PLGA) polymer particles. The formulated product not only elicits primary antibody titers from single dose application but also evokes memory antibody titer against the T independent antigen.

BACKGROUND

PDLLA and PLGA are biodegradable and biocompatible polymers which have been extensively used for various biomedical applications for a long time, especially for drug and vaccine delivery. Polymer particle based vaccine delivery systems provide a viable alternative to multi-dose immunization schedule for many infectious diseases where neutralizing antibody titers provide protective immunity. Particles, particularly made from poly lactide-co-glycolide (PLGA) or PLA, not only work as a delivery system but also provide adjuvant activity.

These polymeric particulate delivery systems have the capacity to promote presentation of the antigen by both MHC class I (MHC I) and MHC class II (MHC II) pathway and thus can activate both humoral and cellular response. Efficient targeting of particulate antigen to the APCs has been reported as a major factor contributing towards the generation of immune response, which requires that the particle size should be between 1-10 μm. The improved immunogenicity of polymer particle entrapped antigen is associated with the continuous delivery of the antigen in to APC and its interaction with macrophages, DC etc for antigen presentation. Immunogenicity of many antigens has been improved while entrapping them in different sized PLA/PLGA particles. However there are no reports on the improved immunogenicity of T independent antigen using PLGA/PLA based polymer particle formulation.

One of the major problems associated with T independent candidate vaccine is the poor generation of memory antibody response after immunization. Memory antibody response is the hall mark of immunity and in absence of it the vaccine has little or no value. To elicit memory antibody, T independent antigens (mostly carbohydrates) are conjugated to a T helper epitope. Conjugation is costly and introduces another candidate antigen to the system. It will be ideal if the memory antibody to carbohydrates antigen can be elicited without conjugation to any other antigenic determinants. In such scenario, entrapments of the carbohydrate antigen in polymer particle alone or in combination of another T helper epitope provide a viable alternative to conjugate.

The innovation described in the patents aims towards the development of carbohydrate vaccine formulation having capacity to elicit memory antibody response. Vi polysaccharide of *Salmonella typhi* is entrapped in polymer particles of desired size and immunized without any adjuvant. Single point immunization of polymer particle entrapped Vi polysaccharide elicit both primary and memory antibody titers in experiments animals.

OBJECTIVE OF INVENTION

The objective of the invention is to provide a vaccine by entrapping carbohydrate antigen such as Vi polysaccharides of *Salmonella typhi* in micron size polymer particle, which has the capability of inducing memory antibody response from a single immunization by generating protective memory antibody response and multivalent display of polysaccharide antigens on biodegradable polymeric particles.

BRIEF DESCRIPTION OF FIGURES AND TABLES

FIG. 1. Scanning electron micrograph of polylactide microparticles (A) and nanoparticles (B) entrapping Vi polysaccharide.

FIG. 2. Immunization protocol for evaluating anti-Vi polysaccharide antibody responses (M-months). Each groups consisted of 6 BALB/c mice and each mouse is primed intramuscularly with 5μg Vi antigen or equivalent amount of particles entrapping Vi antigen dispersed in normal saline. Each group is boosted on $3^{rd}$ month with 1 μg of soluble Vi antigen.

FIG. 3. Antibody responses from immunization of polymer particles entrapping Vi polysaccharides. Six to eight week old six female BALB/c mice per group were immunized intramuscularly with PLA microparticles (entrapping 5 μg Vi antigen, -●- Vi MPs-microparticles), PLA nanoparticles (entrapping 5μg Vi antigen, -▲- Vi NPs-nanoparticles) or 5 μg soluble Vi antigen (-■- soluble) as a single dose. After 90 days, all animals were boosted with 1 μg soluble Vi antigen to evaluate the memory antibody response. A: Comparison of anti-Vi IgM responses from particle formulations entrapping Vi antigen B: Comparison of anti-Vi IgG responses from particle formulations entrapping Vi antigens. Antibody levels were represented as OD at 490 nm at 100× serum dilution (dilution at which OD 490 nm is 3× standard deviation of mean pre-immune OD values). Error bars represent mean±standard error values. * indicates $p<0.001$,  indicate $p<0.01$ whereas ## indicates $p>0.05$. Results are representative of 3 independent experiments with similar trends.

FIG. 4: Anti-Vi polysaccharide antibody responses from polymer particles co-entrapping Vi polysaccharide and carrier protein (TT). Six to eight week old six female BALB/c mice per group were immunized intramuscularly with particles entrapping Vi antigen. After 90 days all animals were boosted with 1 μg soluble Vi antigen to evaluate the memory antibody response. A: Comparison of anti-Vi IgG responses from PLA microparticles entrapping 5 μg Vi polysaccharide (-●- Vi MPs), PLA microparticles co-entrapping 5 μg Vi antigen and carrier protein TT (-▲- ViTTMPs) and 5 μg soluble Vi antigen (-■- soluble). B: Comparison of anti-Vi IgG responses from PLA nanoparticles entrapping Vi polysaccharides (entrapping only 5 μg Vi antigen, -●- Vi NPs), PLA nanoparticles co-entrapping 5 μg Vi antigen and carrier protein TT (-▲- ViTTNPs) and 5 μg soluble Vi antigen (-■- soluble). IgG antibody levels were represented as OD at 490 nm at 100× serum dilution (dilution at which OD 490 nm is 3× standard deviation of mean pre-immune OD values). Error bars represent mean±standard error values. ##

FIG. 5: Effect of Vi antigen/carrier protein ratio as well as carrier pre-immunization on anti-Vi IgG responses from polymer particles co-entrapping Vi polysaccharide and TT. Six to eight week old six female BALB/c mice per group were immunized intramuscularly with particles entrapping 5 µg of Vi antigen. After 90 days, all animals were boosted with 1 µg soluble Vi antigen to evaluate the memory antibody response. A: Comparison of anti-Vi IgG responses from Vi antigen PLA nanoparticles with different antigen/carrier protein ratios. (Entrapping only 5 µg Vi antigen, -●- Vi NPs, and PLA nanoparticles co-entrapping Vi antigen and carrier protein TT in different ratios. [-■- Vi-TT 1:1 soluble mixture, -*- Vi TTNPs 1:1 ratio, -▼- ViTTNPs 2:1 ratio, -✧- ViTTNPs 5:1 ratio, -▶- ViTTNPs 10:1 ratio] B: Comparison of anti-Vi IgG responses from PLA particles co-entrapping Vi antigen and carrier proteins immunized in 6-8 week old BALB/c mice pre-immunized with carrier proteins. PLA nanoparticles co-entrapping 5µg Vi antigen and carrier protein TT (-■- ViTTNPs), physical mixture of 5 µg soluble Vi antigen and carrier protein (-▨- ViTT soluble) and PLA microparticles co-entrapping 5µg Vi antigen and carrier protein TT (-▧- ViTTMPs). IgG antibody levels were represented as OD at 490 nm at 100× serum dilution (dilution at which OD 490 nm is 3× standard deviation of mean pre-immune OD values). Error bars represent mean±standard error values. ## indicates $p>0.05$ FIG. 6: A: Anti-TT antibody responses from polymer particles entrapping only tetanus toxoid or Vi antigen and tetanus toxoid. Six to eight week old six female BALB/c mice per group were immunized intramuscularly with particles equivalent to 5 µg tetanus toxoid. Microparticles entrapping only tetanus toxoid (-■- TTMPs), nanoparticles entrapping only tetanus toxoid (-●- TTNPs), PLA microparticles co-entrapping Vi antigen and carrier protein TT (-⊢- ViTTMPs), PLA nanoparticles co-entrapping Vi antigen and carrier protein TT (-*- Vi TTNPs), physical mixture of 5 µg soluble Vi antigen and TT carrier protein (-✧- ViTT soluble), and soluble TT control (-▼- TT sol). IgG antibody levels were represented as OD at 490 nm at 800× serum dilution (dilution at which OD 490 nm is 3× standard deviation of mean pre-immune OD values). Error bars represent mean±standard error values. *** indicates $p<0.001$. B: In vitro release profile of tetanus toxoid from polymer particles co-entrapping Vi antigen and tetanus toxoid. PLA nanoparticles co-entrapping Vi antigen and TT (-●- ViTTNps) and PLA microparticles co-entrapping Vi antigen and TT (-●- ViTTMPs).

Figure 7:
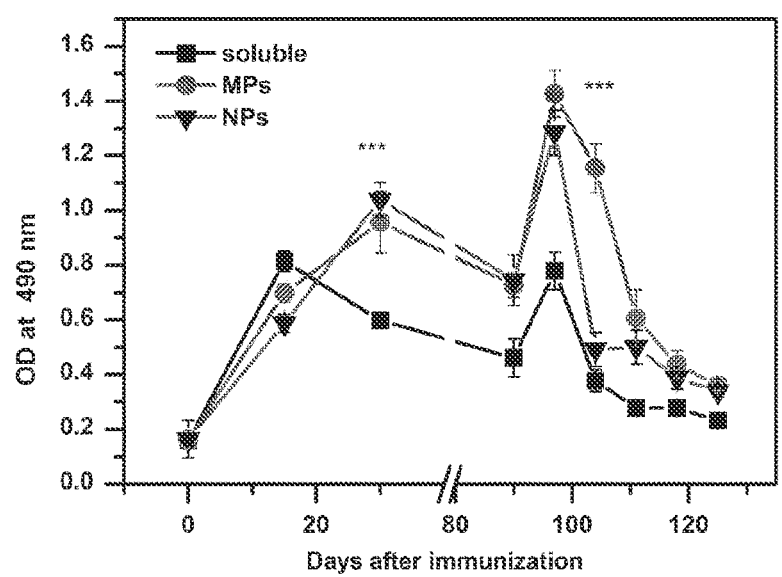
Figure 12:
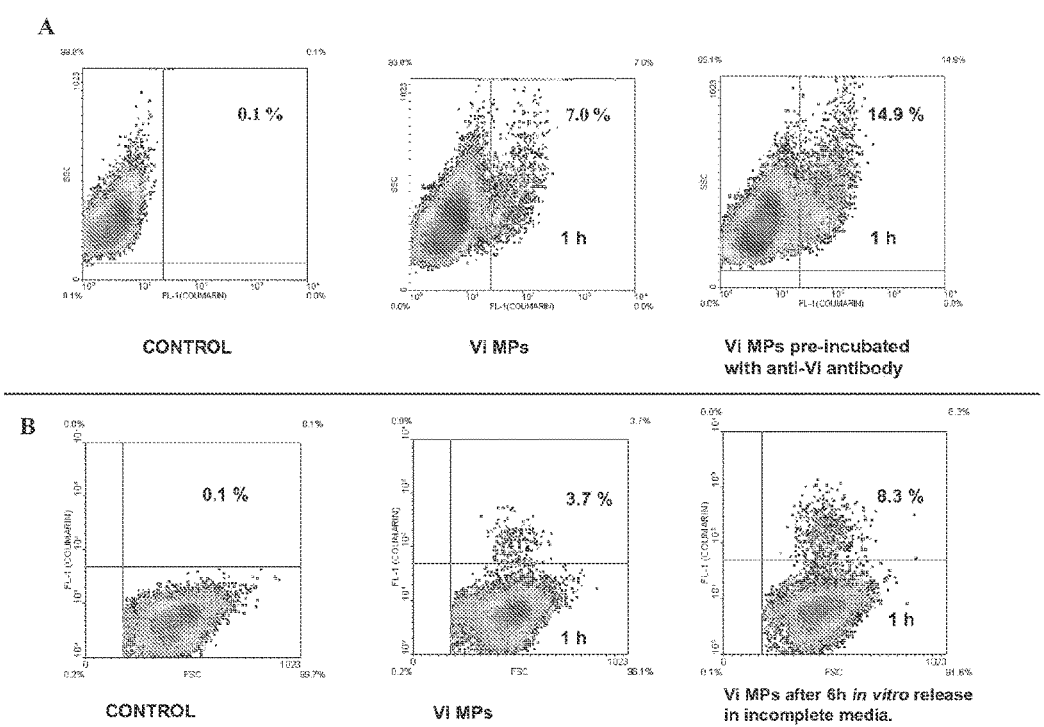

FIG. 7: Memory antibody responses from polymer particles entrapping Vi polysaccharides. Six to eight week old six female BALB/c mice per group were immunized intramuscularly with particles entrapping 5 µg Vi polysaccharide. Soluble Vi polysaccharide based immunization is used as control. After 90 days, all immunized animals were challenged intraperitoneally with 250 CFU live *Salmonella typhi* to evaluate the memory response. Microparticles entrapping only Vi polysaccharide (-●- MPs), nanoparticles entrapping only Vi antigen (-▼- NPs) and 5 μg soluble Vi polysaccharide control (-■- soluble) were used in the study. IgG antibody levels were represented as OD at 490 nm at 100× serum dilution (dilution at which OD 490 nm is 3× standard deviation of mean pre-immune OD values). Error bars represent mean±standard error values. *** indicates p<0.001.

FIG. 8: Anti-Vi polysaccharide memory antibody isotypes elicited by immunization with polymer particles entrapping Vi polysaccharides. Six to eight week old six female BALB/c mice per group were immunized intramuscularly with particles equivalent to 5μg Vi antigen. After 90 days, immunized animals were challenged intraperitoneally with 250 CFU live *Salmonella typhi* to evaluate the memory response. A: Comparison of anti-Vi $IgG_1$ memory responses from Vi entrapped PLA particles. Microparticles entrapping only Vi polysaccharide (-●- ViMPs), nanoparticles entrapping only Vi antigen (-▼- ViNPs) and 5 μg soluble Vi polysaccharide control (-▩- Vi soluble) were used in the study. B: Comparison of anti-Vi $IgG_{2a}$ memory responses from PLA particles entrapping Vi antigen. (-▤- NPs), 5 μg Vi antigen soluble control (-▧- Soluble) and PLA microparticles entrapping 5 μg Vi antigen (-■- MPs) were used in the study. Antibody levels were represented as OD at 490 nm at 100× serum dilution (dilution at which OD 490 nm is 3× standard deviation of mean pre-immune OD values). Error bars represent mean±standard error values. *** indicates p<0.001.

FIG. 9: Effect of particulate nature and antigen surface density on anti-Vi polysaccharide IgG responses from Vi antigen entrapped polymer particles. Six to eight week old six female BALB/c mice per group were immunized intramuscularly on day zero with particles equivalent to 5 μg Vi antigen. After 90 days of priming, all animals were boosted with 1 μg soluble Vi antigen to evaluate the memory response. A: Comparison of anti-Vi IgG responses from physical mixture of dummy polymeric particles and soluble Vi antigens. (-▩-) Physical mixture of dummy PLA nanoparticles and 5 μg Vi antigen, (-▧-) Physical mixture of dummy PLA microparticles and 5 μg Vi antigen and (-□-) 5 μg soluble Vi polysaccharide as control were used in the study). B: Comparison of anti-Vi IgG responses from Vi antigen entrapped PLA microparticles with different surface density of antigens. (-▧-) PLA microparticles with higher surface antigen density and (-▩) PLA microparticles with lower surface antigen density were used in the study. IgG antibody levels were represented as OD at 490 nm at 100× serum dilution (dilution at which OD 490 nm is 3× standard deviation of mean pre-immune OD values). Error bars represent mean±standard error values. *** indicates p<0.001.

FIG. 10: Phagocytic uptake of fluorescent labeled polymer particles entrapping Vi polysaccharide. 50 μg/ml of polymer particles were incubated for different duration with $0.5\times10^6$ murine macrophages. X-axis represents FL-1 channel where the particle associated fluorescence is measured. The percentage of cells in upper right quadrant indicates extent of phagocytosis. Plain MPs: dummy microparticles, ViMPs: microparticles entrapping Vi antigen.

FIG. 11: Inhibition of phagocytic uptake of polymeric particles by Vi polysaccharides in murine macrophage cell line J774A.1. Flowcytometric analyses of macrophages after incubation for defined time points were carried out to evaluate the particle associated fluorescence. 30,000 cells were counted and particle associated fluorescence is analyzed on FL-1 channel (coumarin-6 excitation falls on FL-1 flow channel of BD-LSR). FL-1 positive cells were counted and represented as percentage of cells that phagocytosed the particles. Coumarin-6 labelled fluorescent dummy microparticles (-■- MPs) and coumarin-6 labelled fluorescent microparticles entrapping Vi antigen (-●- MPs) were used in the study. A: Comparison of time dependent changes in the percentage of phagocytic uptake by murine macrophages. B: Comparison of concentration dependent changes in the percentage of phagocytic uptake by murine macrophages.

FIG. 12: Effect of Vi polysaccharides on the surface of polymer particles in inhibiting phagocytic uptake of polymer particles. A: Comparison of phagocytic uptake of Vi MPs by murine macrophages after pre-incubation with anti-Vi antibody. B: Comparison of phagocytic uptake of ViMPs after six hours of in vitro release in incomplete media prior to the incubation with murine macrophages. Flowcytometric analyses of macrophages after incubation for defined time point were carried out to evaluate the particle associated fluorescence. 30,000 cells were counted and particle associated fluorescence is analyzed on FL-1 channel. FL-1 positive cells were counted and represented as percentage of cells that phagocytosed the particles. Coumarin-6 labelled fluorescent microparticles entrapping Vi antigen (ViMPs) were used in the study.

Figure 13:
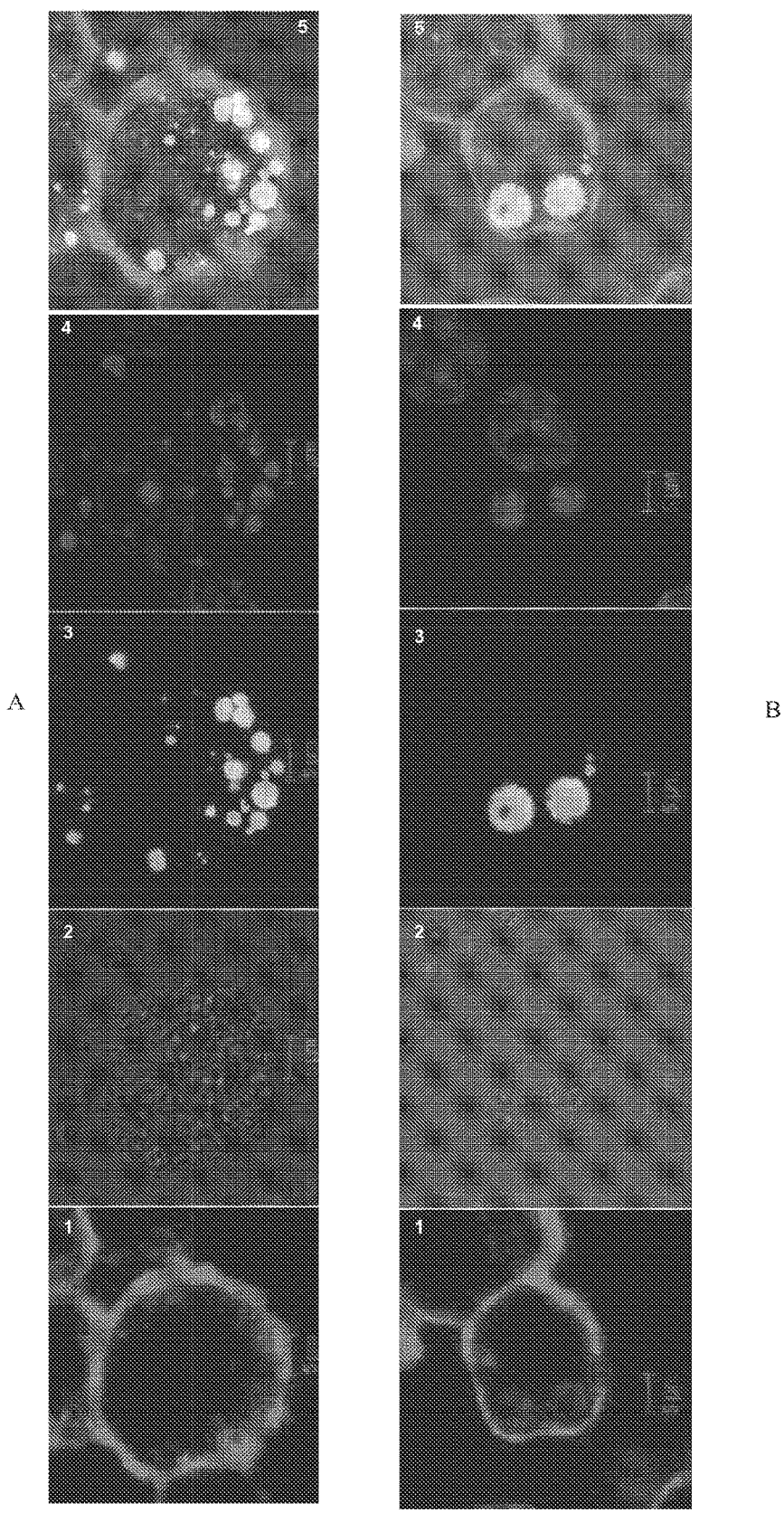

FIG. 13: Phagocytic uptake of coumarin labelled nanoparticles by murine macrophages (J774A.1). GREEN: coumarin associated fluorescence of polymeric particles, RED: F-actin stained with rhodamine-phalloidine, BLUE: Cell nucleus stained with DAPI. Second panel is phase image and fifth panel is merged image of all channels. A: images of cells with phagocytosed nanoparticles and B: images of cells with phagocytosed microparticles (All images were taken at 24 h).

Figure 14:
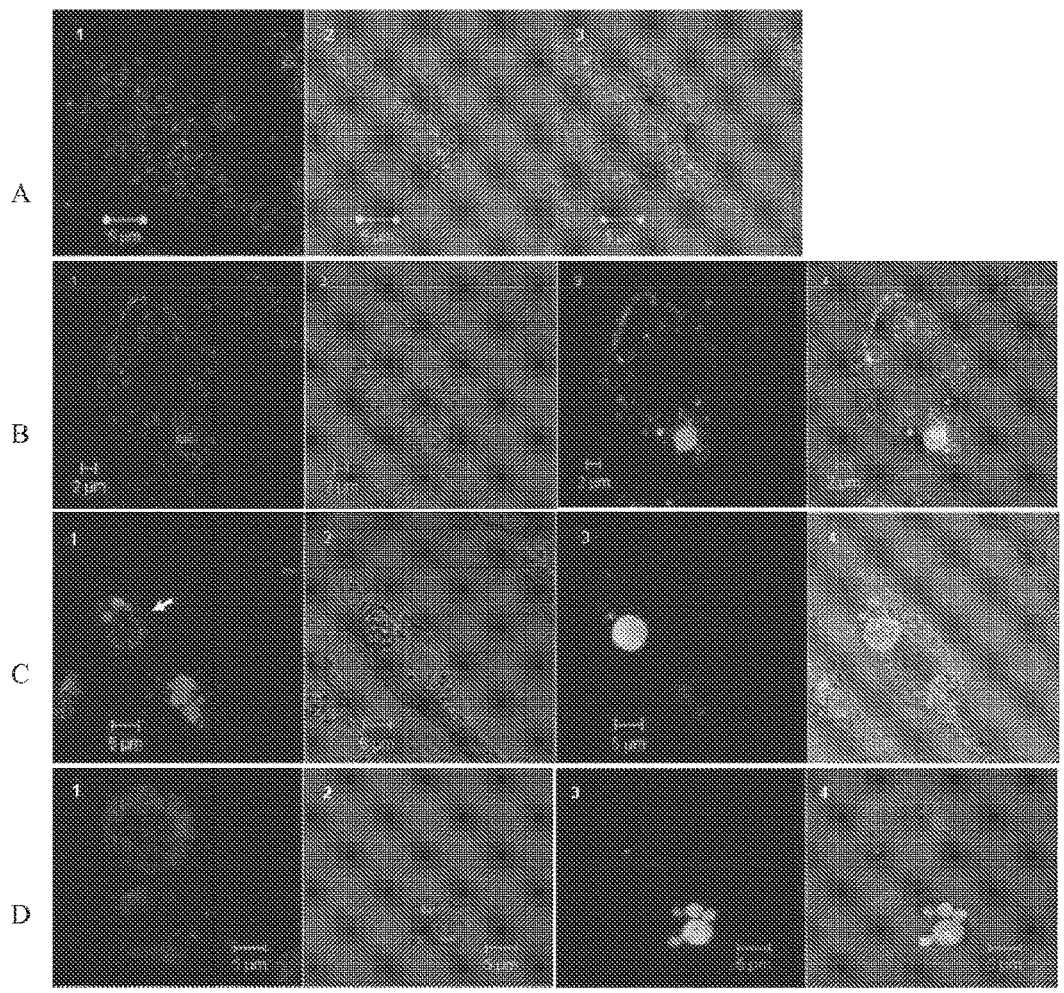

FIG. 14: Intracellular localization and lysosomal remodeling of murine macrophages due to uptake of polymer particles by phagocytosis. A: Lysosomes of untreated control cells B: Co-localization of phagocytosed plain nanoparticles and lysosomal compartments, C: Co-localization of phagocytosed plain microparticles and lysosomal compartments D: Cells which phagocytosed Vi microparticles. White arrow in panel C indicates co-localization of lysosomes and fluorescent particles. GREEN : coumarin associated fluorescence of polymeric particles, RED: lysosomal compartments stained with lysotracker red, BLUE: Cell nucleus stained with DAPI. Second panel is phase image and fifth panel is merged image of all channels (All images were taken at 24 h).

Table 1A: Optimized formulation and process parameters for entrapment of Vi antigen, IAP (Internal aqueous phase), OP (organic phase) and EAP (external aqueous phase)

Table 1B: Optimized formulation constituents used for entrapment of Vi antigen in polylactide micro and nanoparticles. IAP (Internal aqueous phase), EAP (external aqueous phase), PDI (polydispersity index) & span (Vd $0.9-Vd_{0.1}/Vd_{0.5}$)

Table 2: Details of polymer particle formulations co-entrapping tetanus toxoid and Vi polysaccharide antigens.

SUMMARY OF THE INVENTION

Accordingly, the present invention provides a vaccine by entrapping carbohydrate antigen such as Vi polysaccharides of *Salmonella typhi* in a micron size polymer particle like poly (DL) lactide (PDLLA) and polylactide-co-glycolide (PLGA), which has the capability of inducing memory antibody response from single point immunization by generation of protective memory antibody response by multivalent display of polysaccharide antigens on biodegradable polymeric particles. The formulated product not only elicits primary antibody titers from single dose application but also evokes memory antibody titer against the T independent antigen.

DETAILED DESCRIPTION OF THE INVENTION

In general, the polysaccharide antigens are thymus-independent (TI) antigens. Hence, anti-polysaccharide antibody responses are weak and are characterized by lack of memory, isotype restriction and delayed ontogeny. For the first time, we report the generation of protective memory antibody response by the multivalent display of polysaccharide antigens on biodegradable polymeric particles. The Polylactide (PLA) polymer particles entrapping *Salmonella typhi* Vi capsular polysaccharide antigen promote isotype switching and induced polysaccharide specific memory antibody response from a single dose immunization in the tested animals.

PLA nanoparticles as well as microparticles entrapping Vi polysaccharides elicited high IgG titer in comparison to the soluble immunization. Immunizations with particles co-entrapped with both Vi polysaccharide and tetanus toxoid did not improve the anti-polysaccharide antibody responses. Lower antibody response from co-entrapped formulation is mostly due to inhibition of particle phagocytosis by the macrophages. Immunization using polylactide particles entrapping only Vi polysaccharide with higher density at surface elicited highest secondary antibody response as well as promoted isotype switching.

The vaccination potential of particle based immunizations is further confirmed by the generation of quick memory antibody responses while challenging the immunized animals with live *Salmonella typhi*. Improved immunogenicity of Vi polysaccharide entrapped in polymer particle correlated well with its in vitro uptake and antigen delivery in macrophage cell lines. This approach provides a multivalent display of polysaccharide antigen using polymer particles and elicits protective memory antibody response without conjugation to a carrier protein.

The kit according to this invention comprises compositions or vaccines in relation to the method of immunization proposed. The kit according to the invention therefore comprises a container containing various containers containing the compositions or vaccines and advantageously, and optionally, an explanatory brochure including useful information for administration of the said compositions or vaccines.

When introducing elements disclosed herein, the articles "a", "an", "the", and "said" are intended to mean that there are one or more of the elements unless the context dictates otherwise. For example, the term "a compound" and "at least one compound" may include a plurality of compounds, including mixtures thereof.

The terms "comprising", "having", "including" are intended to be open-ended and mean that there may be additional elements other than the listed elements. As is understood by the skilled person, administration of a vaccine can be done in a variety of manners. For example, administration may be done intramuscularly, subcutaneously, intranasally, intradermaly, intrabursally, orally, as well as combinations of such modalities or as decided by the physician. The dose of the vaccine may vary with the size/age of the intended vaccination subject.

It is an important embodiment to provide a vaccine by entrapping carbohydrate antigen such as Vi polysaccharides of *Salmonella typhi* in a micron size polymer particle like poly (DL) lactide (PDLLA) and polylactide-co-glycolide (PLGA), which has the capability of inducing memory antibody response from single shot immunization by generation of protective memory antibody response with multivalent display of polysaccharide antigens on biodegradable polymeric particles.

Another embodiment of this invention is to provide a formulated product that not only elicits primary antibody titers from single dose application but also evokes memory antibody titer against the T independent antigen.

Yet another objective of the invention is to improve the immunogenicity of T independent antigen by entrapping them in polymer particle of different sizes.

Further embodiment of the invention is to entrap polysaccharide based antigen in polylactide particle while protecting the immunogenicity of the antigen.

Still another objective of the invention is to use polymer particle based polysaccharide vaccine formulations to achieve improve antibody response without any additional adjuvant.

Another embodiment of this invention is that memory antibody response is generated from carbohydrate antigen from single point immunization.

Yet another objective of the invention is that the vaccine induces immunological memory without getting conjugated to T helper epitopes.

The entrapping polymer particles, polylactide-co-glycolide (PLGA) or polylactide (PLA) are extensively used in the development of single dose vaccines [1]. These particulate vaccine delivery systems not only deliver antigen in a controlled manner mimicking natural vaccination, but also provide adjuvant activity [2-4]. Recent reports suggest that these delivery systems improve the immunogenicity of the entrapped antigens by actively interacting with antigen presenting cells [5, 6]. These delivery systems can be tailor made with diverse biomaterial properties like surface morphology, geometric size, shape and porosity which are reported to be important for eliciting immune response [6-10]. Submicron size polymer particle based delivery systems offer higher surface area to volume ratio which is ideal for multivalent presentation of ligands to the immune system [11]. Many nanoparticle based delivery systems like polymeric particles, liposomes, inorganic particles have been widely used for multivalent presentation of ligands to biological systems [12-15]. Apart from improving the immunogenicity of the entrapped antigen, it has also been reported that polymer particle based vaccine delivery system elicit improved memory antibody response from single point immunization [7]. The memory antibody response can be further improved by facilitating interactions of these particles with dendritic cells (DCs) using C-Type lectin receptors [16]. Recently, these polymer particles have been designed to do multifunctional work such as artificial antigen presenting cells as well as octafunctional activities [17, 18]. Unlike protein antigens, most polysaccharide antigens elicit antibody responses largely without the need for T-cell help (i.e., they are thymic-independent, or TI antigens). In fact, they directly interact with polysaccharide-specific B-cells which differentiate into plasma cells to produce antibodies. One of the successful carbohydrate vaccines is Vi capsular polysaccharide based vaccine against *Salmonella typhi* infections. *S. typhi* expresses the surface-associated Vi polysaccharide antigen which is a linear polymer of 1, 4(2-deoxy)-2-N-acetylgalacturonic acid variably O-acetylated at the C3 position [19, 20]. Antibodies (Abs) to Vi protect against *S. typhi* infection and vaccines based on purified Vi antigen have been licensed for use in many countries and have consistently shown an efficacy of over 60% in adults in typhoid endemic areas [21-23]. Protection offered by Vi polysaccharide based vaccine is for short duration as it does not elicit memory antibody response. Thus, vaccines need booster immunization in every 3-5 years [21, 24].

Most of the polysaccharide antigens like Vi-antigens are large, multivalent molecules. This multivalency enables them to induce multiple domains of highly cross-linked membrane (m) Ig which has been shown to effect high levels of B-cell activation [25]. Since prolonged contact of the antigen with (m) Ig and subsequent persistent B-cell signalling are important for eliciting an anti-polysaccharide response, it would be interesting to evaluate the possibility of presenting these antigens on biodegradable particles. This would immobilize the polysaccharide antigens on the particle surface and promote B-cell receptor cross linking and thereby improve anti-polysaccharide antibody responses.

Considering the above details, the current study aim to improve the immunogenicity of Vi polysaccharide by entrapping and delivering them using biodegradable polymer particles. To date, immunogenicity of several candidate protein vaccines have been enhanced by delivering them using polymeric particles [6, 7, 26, 27]. However, so far there is very little information available on immune response from biodegradable polymeric particle based delivery systems entrapping polysaccharide antigens.

Many polysaccharide-based vaccines have additional drawbacks that they do not induce protective immune responses in infants under the age of two [28, 29] and fail to induce isotype switching, affinity maturation and memory antibody responses [30]. Many approaches like conjugate vaccines, neoglycoconjugates, peptidomimetics etc have been developed to circumvent the T-lymphocyte independent property of polysaccharide antigens [28, 31].

In a glycoconjugate vaccine, the polysaccharide antigen is covalently linked to a carrier protein making it a single physical entity and this process profoundly improves the immunogenicity of the polysaccharide antigen. In the resulting conjugate, the protein carrier offers the necessary T cell help for the B cell and the immunogenicity of the polysaccharide is greatly enhanced [28, 29]. But this conjugation process is dependent on limited functional groups, and the success of the conjugate vaccine depends on many factors like the carrier-antigen ratio and immunological properties of the carrier [32, 33]. To address these limitations, the current study also explores the possibility of co-entrapping carrier protein and the polysaccharide antigen in the same PLA particles to make it a single physical entity for immunization. The overall objective is to improve the immunogenicity of Vi polysaccharide using polymer particle based delivery system. Accordingly, the results are of indication that polymer particle based vaccine delivery system improves the immunogenicity of T independent antigens considerably from a single immunization dose.

The invention is now illustrated by various examples and accompanying drawings, which are not meant to limit the scope of the invention in any manner All embodiments that may be obvious to a skilled person would fall within the scope of the present invention.

EXAMPLES

1. Materials and Methods
   a. PURASORB poly-DL-lactide (PLA) (45 KDa) is purchased from PURAC (PURAC Biochem, Holland).
   b. Vi capsular polysaccharides were from Bharath Biotech Pvt. Ltd, Hyderabad, India
   c. Tetanus toxoid (TT) (3000 Lf/mL~22.7 mg/mL) from Biological Evans Pvt. Ltd., Hyderabad, India.
   d. Alum (2% w/v Al-hydrogel) from Brenntag Biosector, Denmark.
   e. Fluorescein isothiocyanate-conjugated bovine serum albumin (FITC-BSA), mouse serum albumin (MSA)

and polyvinyl pyrrolidone (PVP), MW 30,000 kDa were from Sigma Chemicals, USA.
f. 6-Coumarin from Polysciences, Warrington, USA.
g. Dulbecco's modified Eagle's medium (DMEM), fetal calf serum (FCS) and Roswell Park Memorial Institute (RPMI-1640) medium were from Invitrogen Corporation USA;
h. Micro-BCA protein assay kit from Pierce, USA.
i. HRP-conjugated Goat anti-mouse IgG from Santacruz, USA.
j. HRP-conjugated anti-mouse IgG1 and anti-mouse IgG2a antibodies were from AbD Serotec, USA.
k. Rhodamine phalloidin, DAPI and Lyso Tracker Red-(red fluorescent dye) were from Molecular Probes, Eugene, Oregon, USA.
l. Glass fiber filter, printed filtermat A, from Wallac, Finland.

2. Preparation of Poly (D, L-lactide) (PLA) Particles Entrapping Vi Antigens

PLA polymer particles were prepared using w/o/w double emulsion solvent evaporation method [26]. Briefly, internal aqueous phase (IAP) containing Vi antigen (10 mg/ml), 0.7% W/V $CaCl_2$ and 1% v/v Tween 20 is emulsified in organic phase (OP) (50 mg/mL PLA solution in dichloromethane) by sonication (20 W, 40% duty cycle, 20 cycles) (Bandelin probe Sonifier 450, USA). The resulting primary emulsion (W/O) is added drop wise to external aqueous phase (EAP) containing 2% (w/v) PVP in deionized water and homogenized (10,000 rpm for 10 min) using a homogenizer (Polytron, KINEMATICA, Switzerland) for MPs and sonicated (20 W, 40% duty cycle, 20 cycles) for preparation of NPs. The resulting particles were collected by centrifugation (15,000 rpm, 20 min), and lyophilized to obtain free-flowing powder.

Dummy particles were prepared using the same method without adding any antigen in IAP.

For the preparation of fluorescent particles either 50 µL of 6-coumarin dye (1 mg/mL in dichloromethane) is added to OP during primary emulsion step, or FITC-BSA (10 mg/mL) is taken in IAP as the antigen. Different sized fluorescent and Vi-entrapped particles were prepared by varying energy input and OP to EAP volume ratio as described earlier [6].

For preparing particles co-entrapping both TT and Vi polysaccharides, both were dissolved in the internal aqueous phase. Ratio of Vi and TT in the internal aqueous phases is varied to prepare particle co-entrapping different concentrations of Vi and or TT. The presence of both the antigens in the same polymeric matrix is confirmed using flowcytometry after immunolabelling the particles with antibodies against individual antigens.

Particles with higher surface density of polysaccharide antigens were prepared by the same method with slight modifications. In order to adsorb the polysaccharide antigens on the surface of the particles, three different formulation strategies were employed. Either preformed particles were incubated with polysaccharide antigen at different temperatures for surface adsorption or excess polysaccharides were added to the external aqueous phase to coat the particles.

Direct spray drying of the final W/O/W emulsion after adding excess polysaccharide is also explored to increase the polysaccharide density on the particle surface. Surface coating of the particles is confirmed using immunolabelling with anti-Vi antibodies and by zeta potential measurements. Particle batches with highest antigen density were used for immunization studies.

2.1 Characterization of Particle Size, Surface Morphology, Encapsulation Efficiency and Release of Antigen from Particles Size distribution of MPs and NPs were determined using mastersizer hydro 2000S particle size analyzer and Zetasizer from Malvern (UK). Surface morphology is analyzed by scanning electron microscope (SEM) (JEOL, JSM 6100, Tokyo, Japan) after coating the particle surface with gold-palladium over an aluminum stub. Internal structures of particles were analyzed by transmission electron microscope (TEM) (CM 10, Philips, Holland)—after coating the particles with 1% uranyl acetate over a copper grid (Polysciences, Warrington, Pa.). TEM images were obtained using digital imaging software—AMT image capture engine (version 5.42.391). Colloidal stability of the particles is analyzed by zeta potential analysis using Malvern Zetasizer from Malvern (UK).

To measure the protein content of particles, accurately weighed particles were dissolved in acetonitrile to solubilize the polymer while precipitating the encapsulated antigens. Precipitated protein is dissolved in 1% sodium dodecyl sulphate (SDS) solution and estimated using micro-BCA assay. A colorimetric method based on reaction of alkaline hydroxylamine reagent with O-acetyl group is used for the estimation of Vi antigen in the polymeric particles [34]. Antigen loading is calculated as the percent weight of antigen per unit weight of polymer.

For in vitro antigen release studies, known amount (20 mg) of each particle formulation is suspended in 1 ml of PBS (50 mM, pH 7.4) containing 0.02% sodium azide in 1.5 ml microfuge tubes and kept in incubator shaker at 37° C. at 200 rpm. Supernatants were collected at different time intervals after centrifugation at 13,000 rpm for 10 minutes at room temperature and analyzed for antigen content as mentioned above. Fresh PBS is added to each pellet after every withdrawal and incubation is further continued over a period of 12 months.

2.2. Evaluating the Immunogenicity of PLA Particles Entrapping Vi Polysaccharide by In Vivo Studies Immunogenicity of PLA particles entrapping Vi polysaccharide is evaluated in BALB/c mice (six female out bred mice per group). Animals were maintained according to the guidelines established by the Institute Animal Ethics Committee (IAEC) of the National Institute of Immunology (NII), New Delhi. Required dose of particles were weighed and suspended in normal saline just before immunization. Immunization of admixture of particles and alum were carried out by adding 25 µL of alum (aluminum hydroxide gel, 2% w/v) to the required dose of polymer particles per animal. Single dose of soluble Vi antigen (5 µg/animal) is used as control.

To evaluate the contribution of particulate nature of antigen in improving the antibody response, immunization studies were also carried out using physical mixture of dummy PLA particles with 5 µg soluble Vi antigen. Mice were immunized intramuscularly with equivalent amount of Vi polysaccharide entrapped in MPs and NPs with or without alum. Sera were collected at different time intervals through retro-orbital plexus and serum antibody titers were determined as described earlier using ELISA [6]. The result is expressed as anti-polysaccharide IgM, IgG, IgG1 and IgG2a absorbance values for different sized particles at a fixed dilution based on background absorbance from pre-immunization sera.

2.3 Immunization Studies with PLA Particles Co-entrapping Vi Polysaccharide and Protein Antigen (TT) in the Same Particles Immunization studies using particles co-entrapping Vi antigen and TT were carried out with following slight modifications. Details of immunization protocol are given in supplementary 4 (S4). All groups were immunized with amount of particles equivalent to 5 g Vi antigen in normal saline. The weight of particles is normalized according to the dose of Vi antigen. Physical mixture of soluble TT and Vi antigens in normal saline is used as the control. Admixture of Alhydrogel™ -(aluminum hydroxide wet gel suspension) and particles were also immunized in different groups using physical mixture of polysaccharide and alum adsorbed protein as the control. Both anti-Vi and anti-TT antibody responses were evaluated separately by ELISA. To evaluate the effect of co-entrapment in improving the anti-Vi antibody response, comparisons were made between formulations containing only Vi and particles co-entrapping both Vi and TT. The same studies were also carried out separately on animals pre-immunized with alum adsorbed carrier proteins. To study the effect of polysaccharides on antibody response of carrier proteins, separate immunization studies were carried out with co-entrapped formulations. In this ease. anti-TT IgG responses were compared between alum adsorbed protein, particles entrapping only protein and particles co-entrapping both protein (TT) and Vi polysaccharide.

2.4 Immunization Studies Using PLA Particles with Higher Surface Density of Polysaccharide Antigens Immunization studies using PLA particles surface coated with polysaccharide and protein antigens were carried out as described in the section 2.4. All animal groups were immunized with polymer particles in normal saline containing 5 g of Vi polysaccharide. A formulation of entrapped proteins and polysaccharide antigens, in the polymer core and dense polysaccharide on the surface, a physical mixture of soluble TT and Vi antigen is used as the control. Anti-polysaccharide antibody response is evaluated using ELISA and compared between particles with higher and lower surface antigen densities.

2.4.1 Evaluation of In Vitro Stimulation of Lymphocytes by Polymer Particle Entrapped Polysaccharide Antigens Using Splenocyte Proliferation Assays For splenocyte proliferation assay, pathogen-free 6-8 weeks old inbred male BALB/c mice (n=3) were intramuscularly immunized with either Vi antigen entrapped in polymer particles or soluble Vi antigen containing 5 gg antigen suspended in 125 µl saline per animal. Non-immunized group of animals is taken as control. One to two weeks after immunization, splenocytes were isolated from the spleen of the euthanized animals and a single-cell suspension is prepared in RPMI medium. Lymphocytes ($0.3 \times 10^6$ cells per well) were incubated in triplicates with serially double diluted soluble Vi antigen as the recall antigen ranging from 10 µg/100 µl downwards at 37° C. and 5% $CO_2$. No antigen is added for the control group and after 72 hours of incubation, 0.5 µCi $^3$H-thymidine/50 µl RPMI medium is added to each well and incubated for a further 14-16 hours. The plates were then harvested on to a glass fiber filter printed filtermat A, using a Strakon cell harvester and incorporated radioactivity is measured in a liquid scintillation counter (Wallac 1205 Betaplate counter).

2.4.2 Evaluation of Memory Antibody Response from Polymeric Particles Entrapping Vi Capsular Polysaccharide Antigens To evaluate the long lasting memory effect of immunization with polymer particle entrapped antigens, immunization studies were carried out as described above. After three months of primary immunization, all animals were boosted with 1 µg of Vi polysaccharide (⅕th of the primary immunization dose) and the antibody response is evaluated using ELISA. All primed animals were challenged intraperitoneally with 250 CFU live *Salmonella typhi* and anti-Vi secondary antibody response is evaluated by ELISA. All groups were compared for the generation of anti-Vi memory antibody responses.

2.5. In Vitro Phagocytic Uptake Studies Using Fluorescent Particles

In vitro and ex vivo phagocytic uptake and trafficking studies were carried out using 6-coumarin and FITC-BSA entrapped polymer particles in murine macrophage cell line J774A.1 and bone marrow derived dendritic cells. Bone marrow derived dendritic cells were cultured according to earlier reports [35]. For in vitro studies, 25 µl (1 mg/ml) of fluorescent particles (300 nm and 2-8 µm) were added to $0.5 \times 10^6$ J774A.1 cells/3 ml of DMEM medium supplemented with 10% FCS, 100 U/ml penicillin, 100 µg/ml streptomycin and 0.25 µg/ml amphotericin B plated in sterile standard tissue culture grade 6-well plates (Falcon, Becton Dickinson, Franklin Lakes, N.J.) and incubated at 37° C., 5% $CO_2$ for various time points. Cells were washed three times with sterile 50 mM PBS and analyzed using flow cytometry or microscopy. For ex vivo studies, bone marrow derived dendritic cells from 6-8 weeks old pathogen-free female BALB/c mice were treated with fluorescent particles and processed as described above.

2.6. Confocal Laser Scanning Microscopy (CLSM)

CLSM images were obtained by simultaneous scanning of contrasting double-labeled specimens using a Zeiss Confocal LSM510 microscope equipped with Argon-Krypton laser (Carl Zeiss Micro imaging Inc. NY, USA). Macrophages were grown on cover slips inside sterile 6-well tissue culture grade plates and incubated with fluorescent NPs or MPs at 37° C., 5% CO2 for various time points; washed with 50 mM sterile PBS and then labeled with 50 nM rhodamine phalloidin or 50 nM Lyso Tracker™ Red-(red fluorescent dye) at 3TC for 30 minutes and again washed three times with 50 mM sterile PBS (pH 7.4). The cover slip is then placed on the stage of confocal microscope. A representative cell is selected at random and a series of optical sections (Z-sections) were taken in dual filter mode. Images captured in RITC, FITC and dual mode were overlaid to determine localization and co-localization of fluorescent particles.

2.7. Flow Cytometric Analysis of Fluorescent Particle Uptake

Flow cytometric acquisition of fluorescent particle uptake study is performed using a BD-LSR flow cytometer (BD Biosciences, San Jose, USA) with Cell Quest program. The data were analyzed using WinMDI 2.8 (Joseph Trotter, Scripps Institute, La Jolla, Calif.). Macrophage cell suspension ($0.5 \times 10^6$ cells) pre-incubated with fluorescent NPs (25 µg) or MPs (25 µg) for various time points (at 37° C., 5% $CO_2$) is analyzed for presence or absence of internalized fluorescent particles. Extra-cellular fluorescence is quenched using an appropriate dye (0.1% w/v crystal violet or 0.4% w/v trypan blue). Dead cells were excluded in the analysis by staining with propidium iodide. In order to study the effect of Vi polysaccharide on phagocytosis of particles, uptake studies were carried out in presence of anti-Vi monoclonal antibodies (Anti-Vi polysaccharide hybridoma supernatants is a generous gift from Dr. Ayub Qadri, hybridoma laboratory, National institute of Immunology, India). Phagocytic uptake studies were also carried out with fluorescent dummy particles in presence and absence of Vi polysaccharide antigen.

2.8. Statistical Analysis

All immunization experiments were carried out three times. Antibody titers were determined using ELISA and expressed as OD at 490 nm at fixed dilutions. Antibody titers of individual animals (n=6) were estimated in duplicates and their OD at 490 nm were expressed as group mean. At any given time point, the comparisons for statistical significance among the group mean and standard deviation (S.D.) values were made using One-way Analysis of Variance (One-way ANOVA) method, along with Tukey-Kramer multiple comparisons post test according to GraphPad InStat Software Inc. (www.graphpad.com). The post test is recommended when comparisons are made for groups ≥3, to compare pairs of group means. Tukey-Kramer multiple comparisons post test is performed only if p value <0.05. All tests were performed at 95% confidence intervals.

particle size distribution (PSD), antigen release profile and entrapment efficiency (% EE). Optimized formulation and process parameters used for making polylactide based polymer particles entrapping Vi polysaccharides are listed in table 1 (1 a and 1 b).

TABLE 1A

Optimized formulation and process parameters for entrapment of Vi antigen, IAP (Internal aqueous phase), OP (organic phase) and EAP (external aqueous phase)

| | Emulsification process | | Phase volume ratio | |
|---|---|---|---|---|
| Formulations | Primary emulsion | Secondary emulsion | IAP:OP | OP:EAP |
| Nanoparticles | Sonication (40% power output, 1 minute) | Sonication (40% power output, 2 minutes) | 1:25 | 1:4 |
| Microparticles | Sonication (40% power output, 1 minute) | Homogenization (10,000 rpm, 10 minutes) | 1:25 | 1:4 |

TABLE 1B

Optimized formulation constituents used for entrapment of Vi antigen in polylactide micro and nanoparticles. IAP (Internal aqueous phase), EAP (external aqueous phase), PDI (polydispersity index) & span (Vd 0.9 − $Vd_{0.1}/Vd_{0.5}$)

| | Size | | | Chemical constituents used in the final formulation used for immunization | | |
|---|---|---|---|---|---|---|
| Formulations | distribution | PDI/SPAN | % EE | IAP | Organic Phase | EAP |
| Nanoparticles | 327.7 nm | 0.270 | 32.7 + 0.8 | 5-10 mg Vi antigen in 200 μl of 0.7% w/v $CaCl_2$ & 1% v/v Tween 20 | 5 ml of 5% w/v PLA 45 kDa in DCM | 2% PVP in 20 ml 0.7% w/v $CaCl_2$ |
| Microparticles | 2.1-3.6 μm | 0.462 | 61 ± 2.3 | | | |

TABLE 2

Details of polymer particle formulations co-entrapping tetanus toxoid and Vi polysaccharide antigens.

| Sl. No. | Formulation | Antigen | Size distribution | % EE | (Vi) Antigen load |
|---|---|---|---|---|---|
| 1 | Vi Microparticles | Vi Polysaccharides | 2-8 μm | 31.2% | 0.366 μg/mg |
| 2 | Vi Nanoparticles | Vi Polysaccharides | 200-300 nm | 25.6% | 1.54 μg/mg |
| 3 | Vi + TT Microparticles | Vi Polysaccharides + carrier protein | 2-8 μm | 45.2% | 0.876 μg/mg |
| 4 | Vi + TT Nanoparticles | Vi Polysaccharides + carrier protein | 200-300 nm | 37.3% | 0.668 μg/mg |
| 5 | Vi + TT Microparticles With higher surface density of Vi polysaccharide | Vi Polysaccharides + carrier protein | 2-8 μm | 31.2% | 9.1 μg/mg |
| 6 | Vi Microparticles With higher surface density of Vi polysaccharide | Vi Polysaccharides | 2-8 μm | 23.2% | 7.3 μg/mg |

Figure 1:
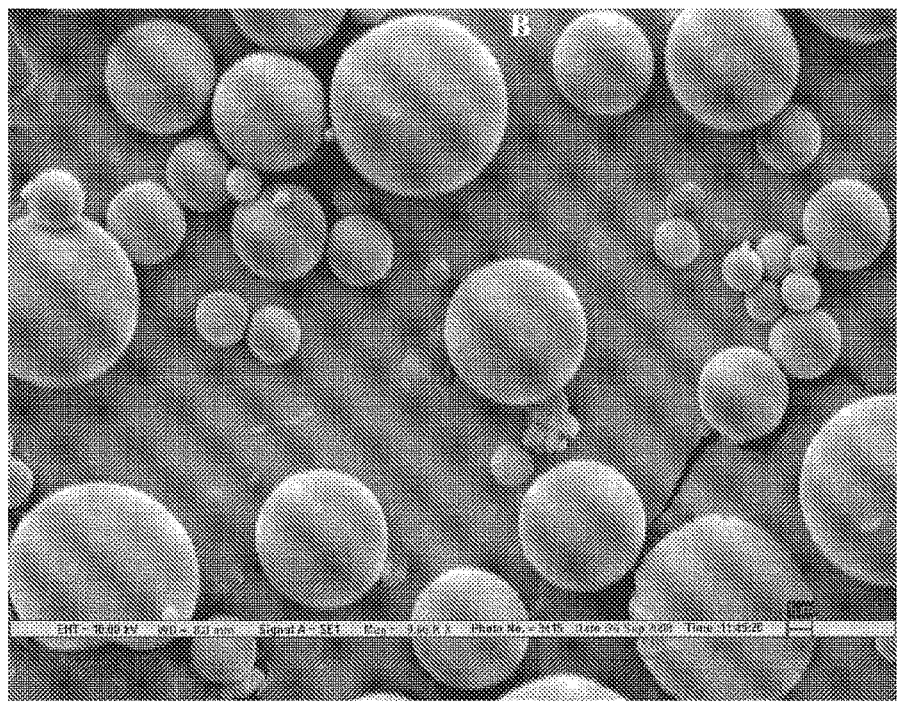
Figure 1:
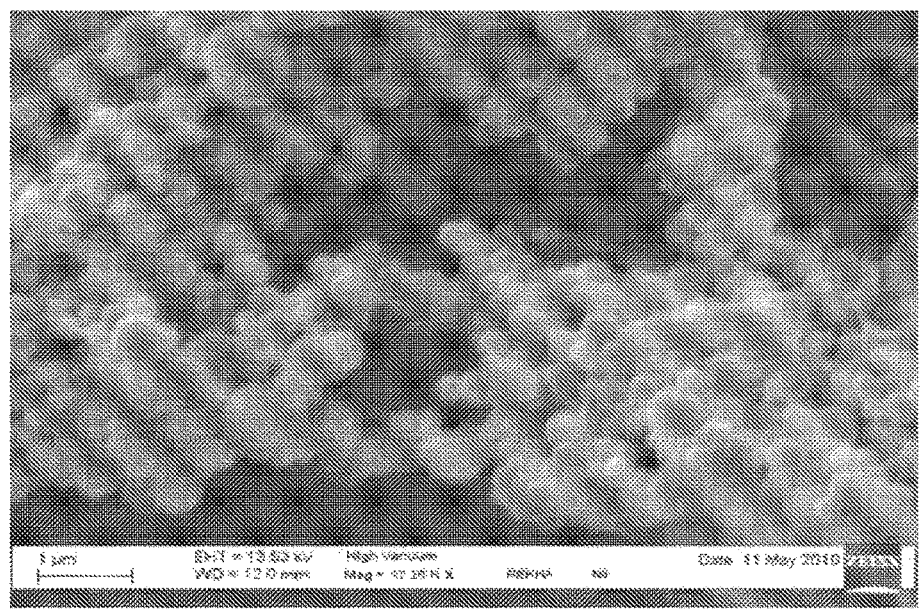

3. —Results 3.1. Formulation and Characterization of Polymer Particles Entrapping Polysaccharide and/or Protein Antigens Double emulsion solvent evaporation method as reported for entrapping protein antigen is used for entrapping polysaccharide antigens (6). Different formulation parameters like phase volume ratio, type of polymer and concentration of emulsion stabilizer were optimized to achieve desired As shown in table 1 (b) and FIG. 1A, microparticles (MPs) prepared using these parameters showed smooth surface morphology (FIG. 1A), narrow size distribution ($Vd_{0.1}$ 1.9-$Vd_{0.5}$ 3.6 μm, SPAN-0.462) and maximum encapsulation efficiency of 61±2.3%. Whereas nanoparticles (NPs) showed 327.7 nm average hydrodynamic size (PDI-0.27), 32.7±0.8% EE and smooth surface morphology (FIG. 1B & supplementary data-S1). The details of polymer particles formulation co-entrapping Vi antigen and tetanus toxoid is presented in table-2. Calcium chloride (0.7% w/v) employed during the formulation of plain Vi-particles is not used in co-entrapped formulations. This helped in reducing calcium chloride induced unfolding of protein antigen at the w/o primary emulsion interphase. It is observed that addition of tetanus toxoid improved the encapsulation efficiency of Vi capsular polysaccharides. This could be due to stabilization of primary emulsion by preferential orientation of protein antigens at the interface between the IAP and organic phase as reported for bovine serum albumin [36]. Phase volume ratio (IAP:OP:EAP) plays a major role in size distribution of particles formed from double emulsion solvent evaporation process [6]. In order to maintain the same phase volume ratio (IAP:OP:EAP) that employed in the preparation of plain Vi particles, the volume of internal aqueous phase is kept same (200 µl). This volume constraint limited the amount of polysaccharide used for entrapment in the internal aqueous phase and resulted in reduced antigen load per mg of polymeric particles (1.54 g/mg for plain ViNPs vs 0.668 g/mg for Vi+TT NPs). Entrapment of both the antigens in the particles is confirmed by surface labeling of particles with mouse anti-Vi IgM and mouse anti-TT IgG antibodies. Dummy MPs were used as the control. Polymer particles were analyzed by flowcytometry for particle associated fluorescence. Particles co-entrapping both TT and Vi polysaccharide showed the fluorescence corresponding to both the antigens in the same population indicating the presence of both TT and Vi polysaccharide on the surface of MPs (supplementary data-S2). Particles with higher Vi antigen surface density were prepared by adding excess Vi antigen (10 mg/ml) in the external aqueous phase during secondary emulsification stage. This promoted slow adsorption of capsular polysaccharide on to the surface of polymer particles during solidification. Higher antigen content per mg of MPs indicated higher adsorption of polysaccharides on to the surface of particles (Table 2, formulation 5 & 6). Surface adsorption of polysaccharide is confirmed further using zeta potential and flow cytometry analysis of particles immuno-labelled with anti-Vi polysaccharide IgM. Zeta potential of coated particles showed higher negative values compared with particles with relatively less surface density of Vi polysaccharide. Particles with higher surface density of Vi polysaccharide showed higher Vi associated fluorescence in flowcytometry (supplementary data-S3). However during formulation of NPs, presence of polysaccharide in EAP induced coalescence of ultra-small globules of W/O/W emulsion. This resulted in size growth of the particles. Thus, only MPs with higher surface adsorbed Vi polysaccharides were prepared and used for the immunization study.

Figure 2:
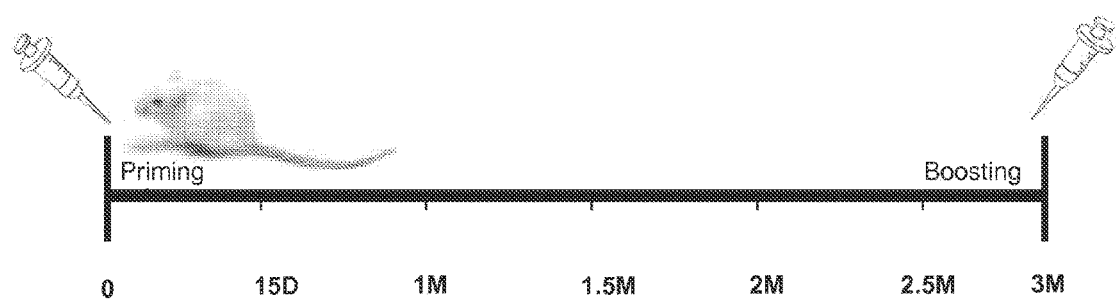
Figure 3:
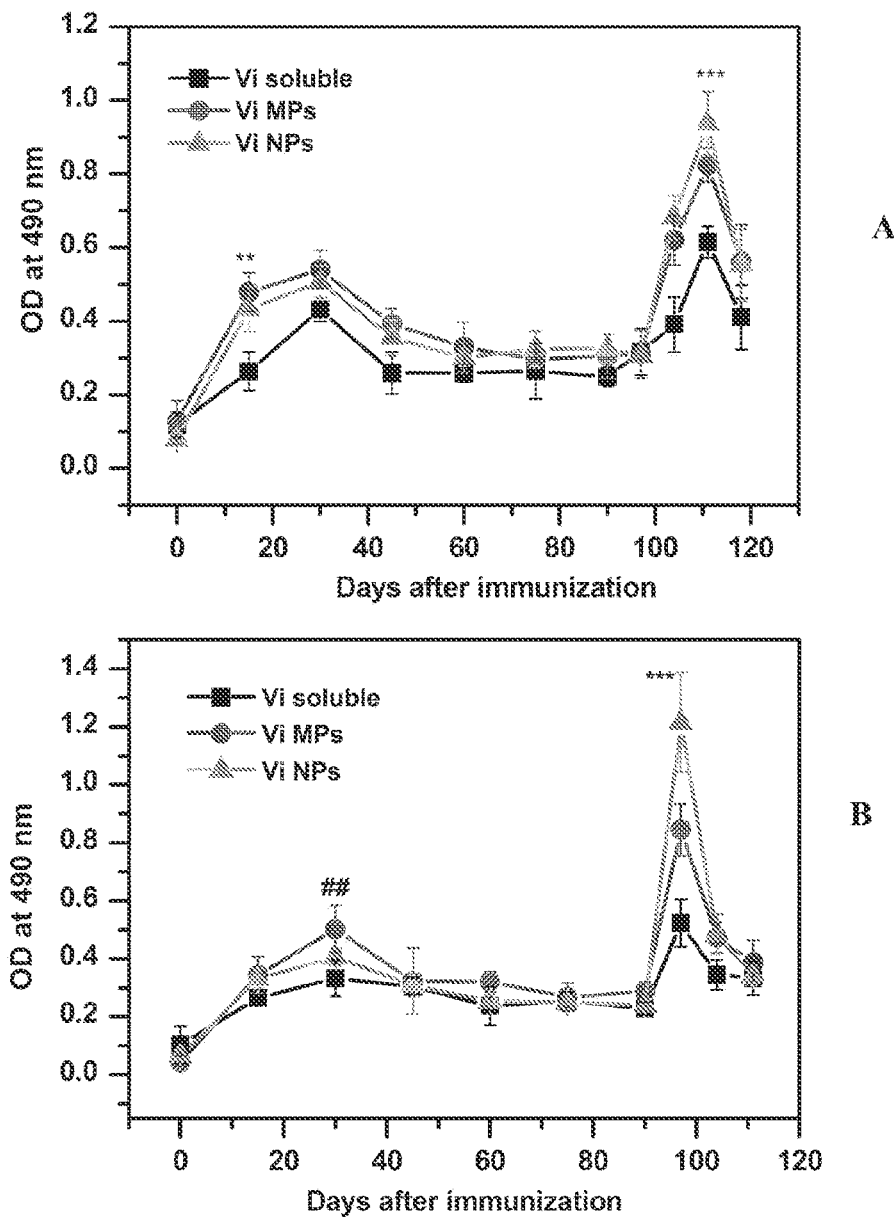

3.2. Anti-polysaccharide Antibody Responses from Polymer Particles Entrapping Vi Antigen Polymer particles entrapping polysaccharide antigens were immunized intramuscularly in BALB/c mice using protocol shown in FIG. 2. Anti-Vi IgG and IgM responses determined using ELISA are shown in FIG. 3 Immunization with polylactide particle formulation entrapping Vi antigen elicited significantly higher anti-Vi IgM response than that observed from immunization with soluble Vi antigen ($p<0.001$ for secondary response and $p<0.01$ for primary response FIG. 3A). Irrespective of the size distribution, antigen entrapped in both NPs as well as MPs induced strong anti-Vi IgM responses. The same trend is observed in the case of anti-Vi IgG responses (FIG. 3B). Considering the opsonophagocytic potential of IgG and its role in protection against encapsulated bacteria, it is important to elicit IgG responses against capsular polysaccharide antigens [28]. As shown in FIG. 3B, compared to soluble immunizations (0.4 peak titer OD values), polymer particles entrapping Vi antigen elicited strong IgG responses (1.2 peak titer OD values, $p<0.001$). This enhanced IgG response is very significant since it improve the immunogenicity of Vi polysaccharide based vaccines. Vi antigen based commercial vaccines being type-2 T-independent antigens, elicit predominantly IgM responses and do not induce isotype switching of antibody responses [37, 38]. However, delivery of Vi antigen through polymer particles induced class switching of antibody response. Polysaccharide vaccines generally induce very weak memory antibody responses. As shown in FIG. 3, the secondary antibody responses in group of animals immunized with Vi entrapped polymer particles were higher than that observed with immunization of soluble Vi antigen ($p<0.001$). It is significant to note that polysaccharide antigens entrapped in both NPs and MPs elicited a stronger memory antibody response. Quick and higher secondary antibody response induced by a $\frac{1}{5}^{th}$ of priming dose indicated that interaction of particles with the B-cells during primary immunization stage is different than that with soluble Vi polysaccharide. The rapid and high antibody recall response suggests that sustained presentation of polysaccharide antigen by polymeric particles promote differentiation of B-cells to memory B-cells and induced class switching of antibody isotypes. These observations are very important in the context of vaccinations against infections caused by encapsulated bacteria.

It has been reported that for protein antigens, as the particle size decreases from micrometer range to nanometer range, antibody titer decreases [7, 39, 40]. Information on such particle size dependent modulation of immune response is not available for polysaccharide antigens. NPs in the range of 300 nm to 600 nm (Z average hydrodynamic size) and MPs (2-8 µm Vd) were used for immunization study. These sizes were selected to differentiate between antibody eliciting potential of NPs and MPs. A size dependent difference in the magnitude of anti-Vi antibody response is observed (FIG. 3). NPs entrapping Vi polysaccharides elicited stronger IgG responses than MPs. Vi antigen entrapped in NPs elicited significantly higher memory antibody responses than microparticles based immunizations (FIG. 3B, $p<0.001$) and no significant differences were observed in the IgM response. These are contrary to the observations reported earlier on size dependent modulation of antibody responses with polymer particles entrapping protein antigens [7, 40]. These differences also point to the diversity which exists in interactions of different antigens with immune system. This also supports the view of optimizing the vaccine delivery systems based on size, shape and release profile for modulating the immune responses [41]. These results open up possibilities of generation of memory antibody titer while entrapping polysaccharide antigens in polymer particles.

3.3. Antibody Responses from Polymer Particles Co-entrapping Vi Antigen and Tetanus Toxoid (TT)

Figure 4:
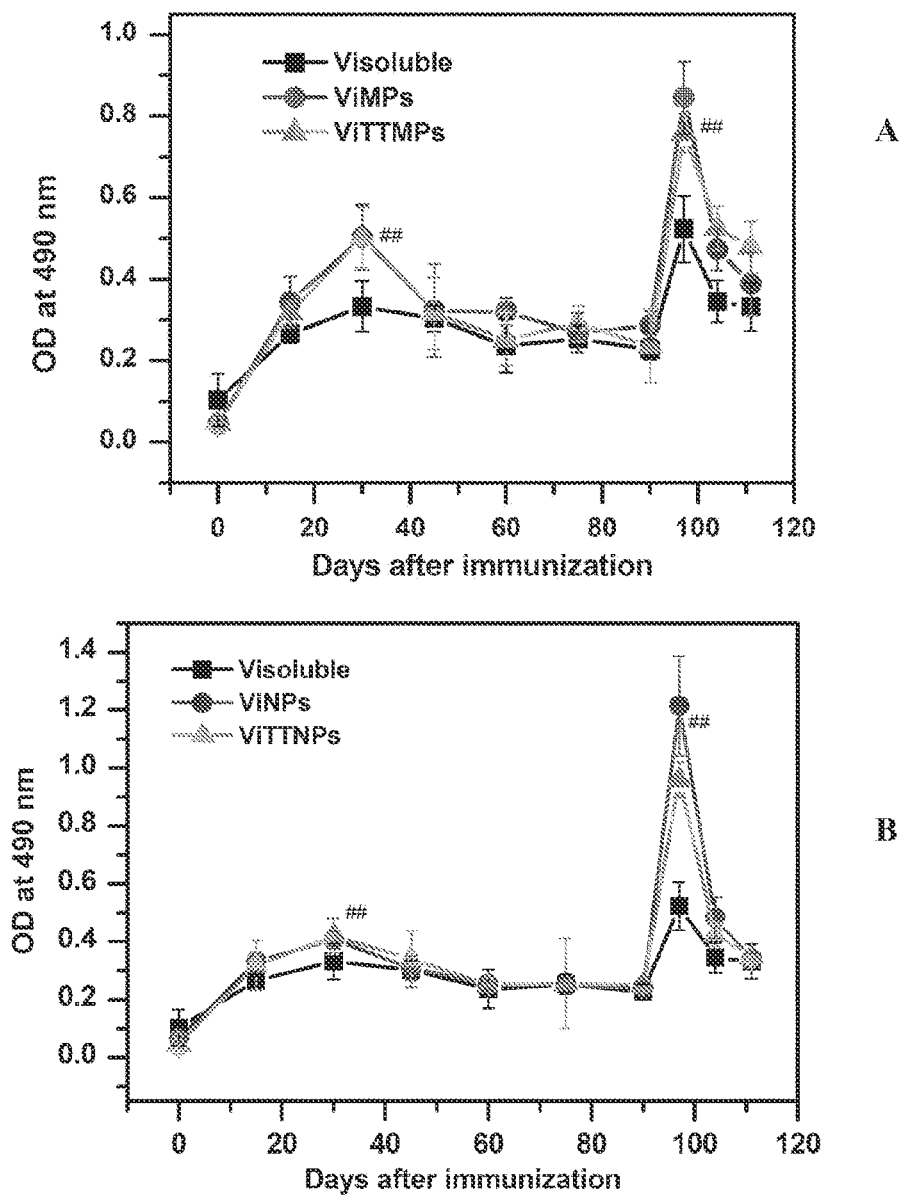

To provide an alternative to glycoconjugate vaccines, immunization studies using particles co-entrapping a carrier protein (tetanus toxoid) and Vi polysaccharide antigen in the same particle is explored. It is observed that for both MPs and NPs, co-entrapment of TT along with Vi polysaccharides resulted in lower antibody titers (FIG. 4). The results in the FIG. 4 A indicated that, immunizing with PLA particles co-entrapping Vi antigen and carrier protein did not significantly improved the IgG responses against the Vi antigen (mean OD 0.82 for ViMPs: MPs entrapping only Vi antigen and mean OD 0.78 for ViTTMPs: MPs co-entrapping Vi antigen and carrier protein TT). Antibody responses were comparable to that observed from particles entrapping only Vi antigen (P>0.05). This effect is seen in primary as well as in secondary antibody responses. The same trend is observed with NPs co-entrapping carrier protein and Vi polysaccharide antigen (FIG. 4 B). The antibody titers from ViNPs entrapping only Vi antigen (mean OD 1.2) is higher than that observed from ViTTNPs co-entrapping both carrier protein and Vi antigen in the same particles (mean OD 0.82 and P>0.05).

The immunological properties of the carrier protein, conjugation chemistry, the carrier-polysaccharide ratio have been reported to either enhance or suppress the antibody responses from the conjugated carbohydrate antigen [42-44]. Thus, the outcome of immune response from glycoconjugate vaccine depends on the ratio of carrier protein and carbohydrate antigen, immunogenicity of the carrier protein, dose of carrier protein and the level of pre-existing immunity against the carrier protein [43, 45]. Additional immunization studies were carried out to elucidate the role of these parameters on the anti-Vi antibody response from polymer particles co-entrapping Vi antigen and tetanus toxoid as a carrier protein. Initially, to study the role of antigen-carrier ratio, NPs with different polysaccharide-TT ratios were prepared and immunized in BALB/c mice. NPs with different TT-polysaccharide ratio were prepared by varying the concentration of TT initially used in the internal aqueous phase. The anti-polysaccharide IgG response is analyzed using ELISA and the results are shown in FIG. 5A. Though the general trend of particles eliciting stronger IgG response than soluble Vi antigen is observed, the co-entrapped polymer particle formulations per se did not improve the anti-Vi IgG antibody responses. It is observed that irrespective of the protein-polysaccharide ratio employed, the particles co-entrapping Vi antigen and TT did not elicit stronger IgG response than particles entrapping only Vi antigen. Pre-existing immunity against an immunological carrier can either enhance the antibody response against the carbohydrate antigen through extending improved T-cell help or can suppress the response through carrier induced epitopic suppression [44, 45]. To study these effects, immunization studies using co-entrapped formulations were carried out in animals pre-immunized with carrier protein (TT). Animals in different groups were initially primed with alum adsorbed 5 μg tetanus toxoid. On 15$^{th}$ day post immunization, when the anti-TT antibody response peaked, all animals were immunized with polymeric particles co-entrapping Vi antigen and tetanus toxoid. The anti-Vi IgG response is monitored and the results are shown in FIG. 5B. It is observed that the polymer particles co-entrapping TT and Vi antigen did not elicit significantly higher IgG response than soluble immunizations. The anti-Vi IgG responses were comparable in all the three groups. The pre-existing immunity against the carrier protein did not improve the anti-polysaccharide antibody responses from co-entrapped formulations. The results reflected the inferiority of polymer particles co-entrapping carbohydrate and protein antigen as an alternative to glycoconjugate vaccines for improved antibody responses. Its failure to elicit stronger response points to the importance of both the antigens to exist as a single covalently linked physical entity. The antibody responses suggest that polymer particle entrapped polysaccharide antigens alone can be a promising vaccination mode for carbohydrate antigens but the potential of co-entrapped formulations to mimic conjugate vaccines is limited.

3.4. Effects of Vi Antigen on Anti-TT Antibody Response from Polymer Particles Co-entrapping Vi Antigen and TT Immunization with protein-conjugated polysaccharide induces protein-specific T-helper (Th) cells, provide help to polysaccharide-specific B-cells. These act as antigen presenting cells for the carrier protein through direct cell-cell contact and cytokine secretion, resulting in B-cell differentiation towards memory or plasma cells [33, 46, 47]. Thus mounting a strong immune response against the carrier is a prerequisite for recruiting CD4$^+$ T-cell help for the polysaccharide. Failure to mount a strong immune response against the carrier protein would lead to absence of expected T-cell help to the carbohydrate antigens. So antibody responses against the carrier protein (anti-TT antibody titer) from immunization with co-entrapped formulations were analysed.

Figure 6:
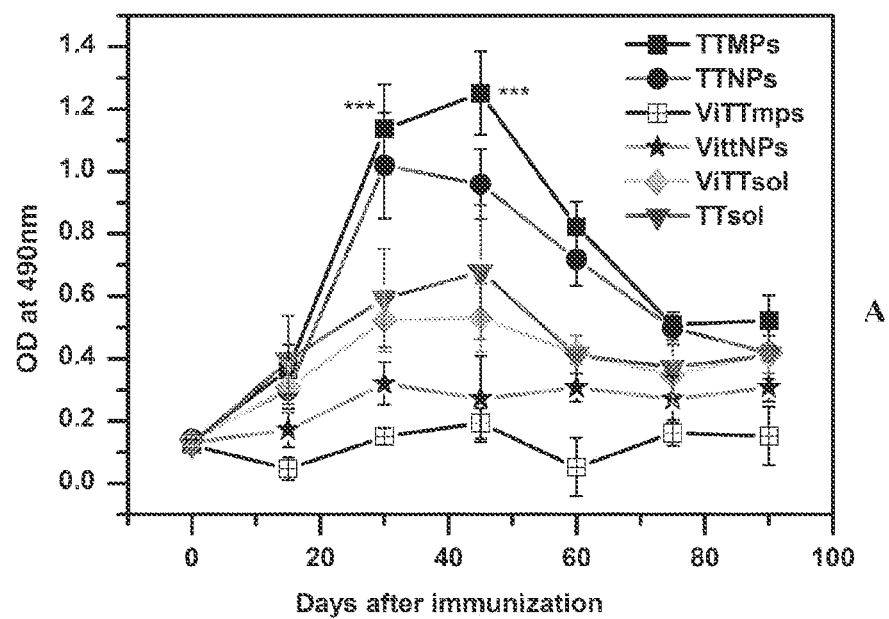
Figure 6:
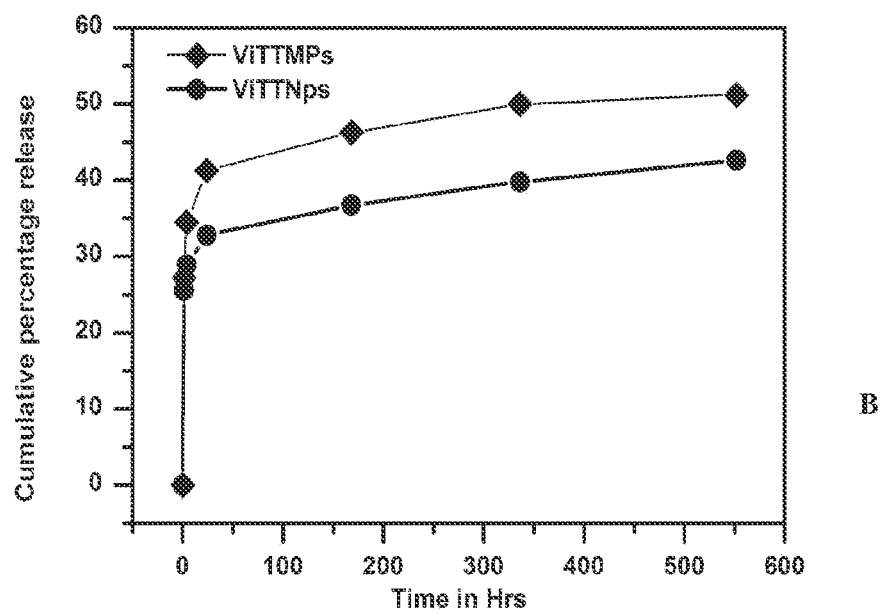

The antibody response against carrier protein (anti-TT antibody titer) while immunizing with co-entrapped polymer particles is shown in FIG. 6. It is observed that, anti-TT IgG responses from animals immunized with co-entrapped formulations were significantly lower than anti-TT IgG response observed with immunizations using particles entrapping only TT and soluble TT. The anti-TT IgG responses were severely hampered and presence of Vi antigen suppressed the anti-TT IgG responses (data not shown). Since all animals were immunized with particles normalized to 5 μg Vi antigen, the antigen load is not equal in all the immunized particles. Since antigen load is a very important parameter which drives the antibody responses from polymer particles, immunization studies were repeated with formulations having equal TT loads (supplementary data S4). The IgG responses clearly indicated that all co-entrapped formulations failed to induce strong anti-TT responses which are inevitable for recruiting CD4$^+$ T-cell help for the polysaccharide component. Immunization with MPs and NPs entrapping only TT elicited stronger IgG response (TTMPs—mean OD$_{490nm}$ 1.2±0.2, TTNPs—mean OD$_{490nm}$ 0.85±0.2,ViTTMPs—mean OD$_{490nm}$ 0.1±0.02, ViTTNPs—mean OD$_{490nm}$ 0.2±0.05 and p<0.001) when compared to particles co-entrapping Vi antigen and TT. The presence of Vi antigen in the particles severely affected the antibody responses to carrier protein. Vi induced suppression of anti-TT IgG responses, explained the failure of co-entrapped formulations in improving the Vi specific IgG responses. The suppression of anti-TT IgG responses by Vi antigen in the co-entrapped formulations would prevent the expected T-cell help from the carrier protein. The suppression of anti-TT IgG response by Vi antigen can be due to many reasons. The presence of Vi antigen and TT in the same polymeric matrix can hamper the release of TT from the particles resulting in reduced availability of TT in the draining lymph nodes. To rule out this possibility, in vitro release profile of TT is analysed and the results are shown in FIG. 6B. Sustained release profile of TT in the presence of Vi antigen is observed. Since the release of TT is not hampered by Vi antigen, the Vi mediated suppression of anti-TT IgG responses could be due to anti-inflammatory and anti-phagocytic effect of Vi antigen. Vi antigen on the capsule of *Salmonella typhi* helps the bacteria to evade phagocytosis and induces anti-inflammatory responses [48]. Efficient generation of anti-TT immune response depends on processing and presentation by antigen presenting cells. In co-entrapped formulations, the presence of Vi antigen on the surface of the particles interfered with the interaction of these particles with APCs. The anti-phagocytic effects of Vi antigen inhibited phagocytic uptake of polymer particles and resulted in suppression of anti-TT IgG responses. Since eliciting a strong anti-TT response is important to recruit T-cell help for Vi antigen, this suppression limited this help to Vi antigen. This explanation of lower antibody response from co-entrapped formulation is supported by the in vitro phagocytic uptake studies of different polymeric particle formulation and is discussed in later sections.

Figure 8:
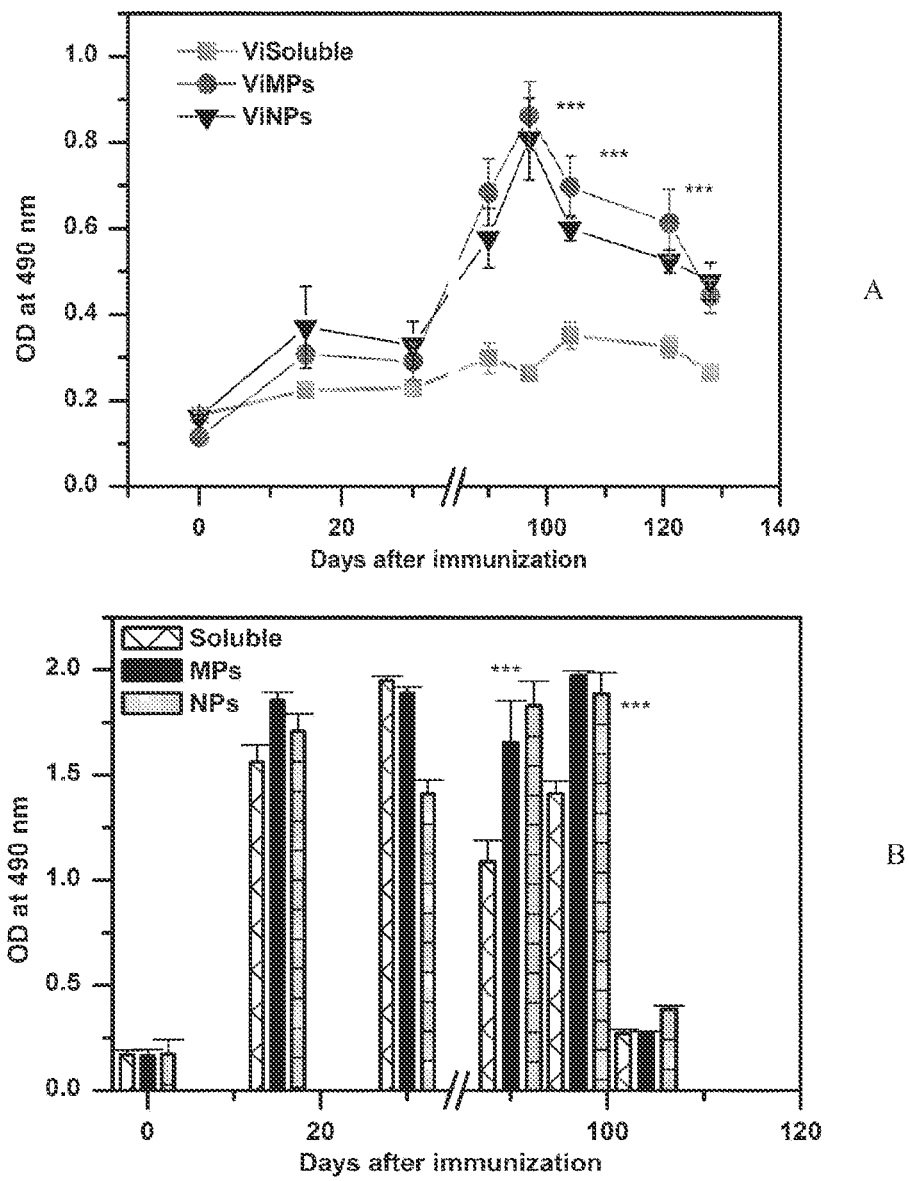

3.5. Challenge Studies with Live *Salmonella typhi* to Evaluate Memory Antibody Responses from Immunizations Using Polymer Particles Entrapping Vi Antigen In order to mimic a real life scenario and to evaluate the antibody responses to a post vaccination infection, challenge studies were carried out with live *Salmonella typhi*. As represented in FIG. 7 immunization with particulate formulations elicited very high IgG responses in comparison to soluble immunizations (MPs mean $OD_{490nm}$ 1.4±0.04, NPs mean $OD_{490nm}$ 1.2±0.05 and soluble mean $OD_{490nm}$ 0.8±0.5 and p<0.001). Vi antigen being a T-cell independent antigen do not produce significant IgG response when immunized in soluble form. But presentation of antigen in a sustained release manner from polymer particles would have promoted prolonged presence of antigen in the draining lymph nodes as well as at the site of injection. This could stimulate the polysaccharide reactive B-cells continuously and induce very high antibody response [49, 50]. Persistence of antigens provides the survival signal for antigen reactive lymphocytes and promotes antibody responses and isotype switching [41, 50]. In order to assess the potential of particulate formulations in promoting isotype switching of antibody responses, anti-Vi IgG1 and anti-Vi IgG2a responses were analysed using ELISA. Antibody responses indicated that particulate immunizations elicited high IgG1 and IgG2a responses (FIG. 8). This is very important considering the opsono-phagocytic role of antibody offering protection against encapsulated bacteria. Moreover, the results in FIG. 8 indicated that, particulate formulations elicited stronger recall response against the *Salmonella typhi* challenge. The anti-Vi IgG recall responses elicited by immunizations with Vi antigen entrapped in polymeric particles were significantly higher than observed with soluble Vi immunizations (p<0.001). This long term recall response in response to the real live pathogen is very important in the context of vaccinations. IgG responses against Vi antigen are protective in nature, help in opsonising the bacteria and promote rapid clearance of the encapsulated bacteria [51, 52]. Since particulate immunizations were successful in mounting strong recall responses, this demonstrated the potential of these systems in improving the immunogenicity of T-independent antigens. Vaccination with polysaccharide antigens generally elicit IgM responses and fail to induce antibody isotype switching [28]. In this context, higher IgG1 and IgG2a responses (FIG. 8) elicited by particulate formulations are very significant and proved the vaccine delivery potential using polysaccharide entrapped PLA particles.

Splenocyte proliferation assays were carried out to confirm the importance of particle nature of polymeric delivery systems in priming the immune system. Thymidine incorporation is used as an indication of splenocyte proliferation and the results are shown in supplementary data S5. The results showed significant enhancement in proliferation rates of splenocytes isolated from mice primed with Vi MPs. This indicated that antigen entrapped in particulate delivery systems effectively primed the immune system and promoted the anti-Vi antibody responses. Efficient priming effect of antigen entrapped MPs helped in mounting an effective recall response.

Figure 9:
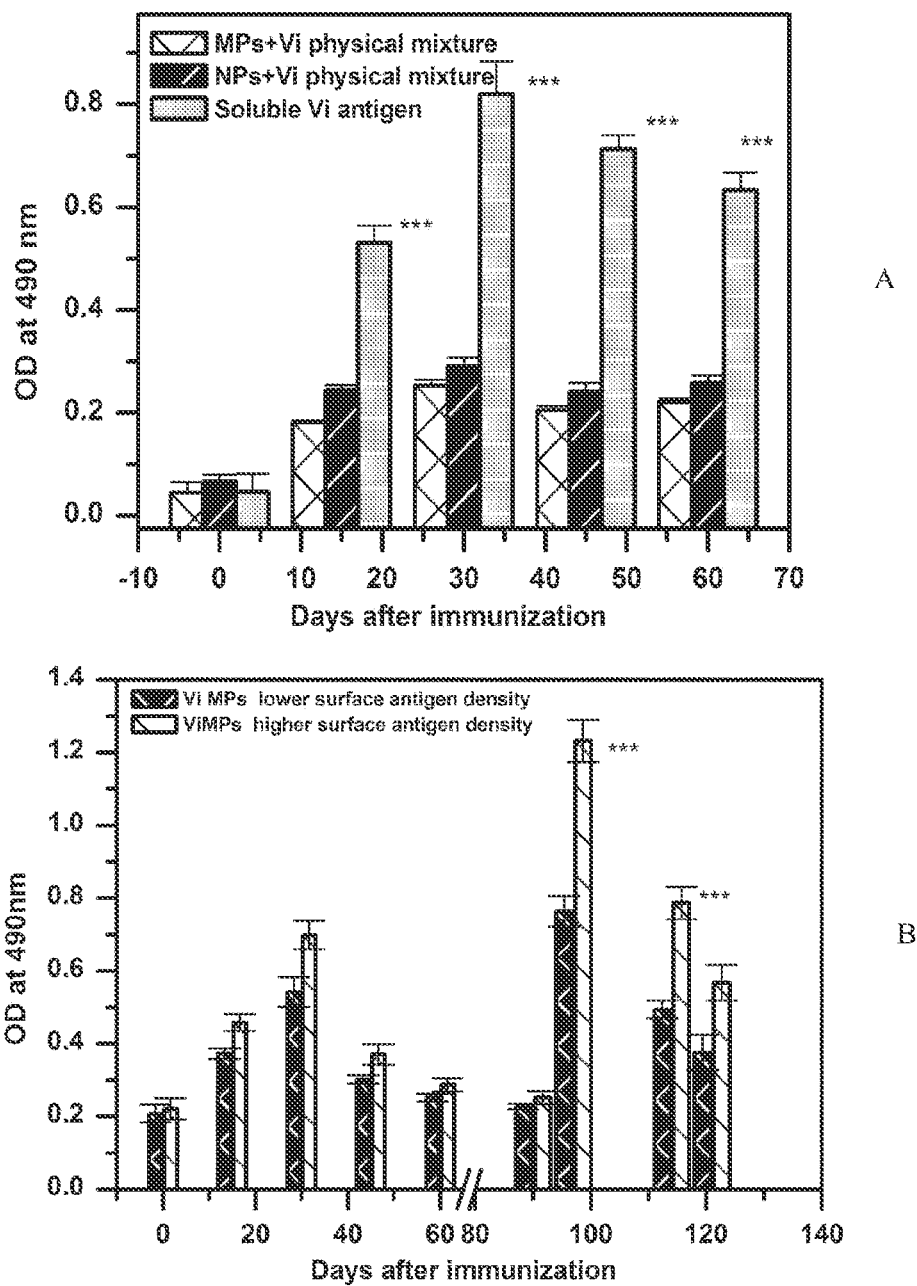

Previous studies have reported that polysaccharide antigens immobilized on latex beads induce strong immune responses than soluble immunizations [53]. Significantly higher IgG responses induced by Vi antigens entrapped in PLA particles as observed in this study could be due to 'the particulate nature' of polymeric delivery systems. Antigens immobilized on particles can display an array of important structural elements which are essential for B-cell recognition. These immobilized antigens promote multivalent interaction of B-cell receptor and polysaccharide antigens. B-cells are reported to interact with immobilized antigens effectively than soluble antigens [53]. To elucidate the contribution of particulate nature, immunization experiments were carried out with physical mixture of dummy particles and Vi antigens, taking Vi antigen entrapped particles and soluble Vi antigen as the control. All animals were immunized with 5 µg Vi antigen or particles equivalent to 5 µg Vi antigen. Amount of dummy particles immunized per animals were normalized according to the amount of antigen entrapped particles. It is observed that the anti-Vi antibody responses were significantly reduced and were lower than that observed with soluble Vi immunizations (FIG. 9A). The general effect of particle induced enhancement in anti-Vi antibody responses is abrogated. Physical mixtures of dummy particles and soluble antigens failed to improve the anti-Vi IgG responses. This indicated that entrapment of antigen in the polymeric particles promote strong antibody responses. Irrespective of the size, both NPs as well as MPs administered as a physical mixture with antigen failed to improve the anti-Vi IgG responses. This suggested that the particulate nature as well as the sustained release of antigens offered by polymeric delivery systems is very important for augmenting anti-Vi antibody responses.

3.6. Immunization Studies Using Polymer Particles with Higher Surface Density of Polysaccharide Antigens Polysaccharide antigens are constituted of repeated sugar motifs which cross-link the B-cell receptors and activate antigen specific B-cells independent of $CD4^+$ helper T-cells. B-cells bind effectively to antigens immobilized on particles or tethered to the cells than soluble antigens [53]. Thus, antigen entrapped polymer particles can promote antigen binding to B-cell receptors (BCRs) and enhance cross-linking of BCRs resulting in improved antibody response. This will promote B-cell activation and associated antibody responses. To evaluate this possibility, particles with higher surface density of Vi antigen were prepared and immunized in BALB/c mice. Higher surface density of Vi antigen is confirmed using flowcytometry after labelling with anti-Vi antibody (supplementary data S3). Anti-Vi IgG responses were determined using ELISA and the results are shown in FIG. 9B. It is observed that particles with higher surface density of Vi antigen elicited higher anti-Vi IgG responses (0.7 Mean $OD_{490nm}$ for MPs with lower surface density Vs 1.2 mean $OD_{490nm}$ at first week after boosting p<0.001). More importantly the memory antibody titer is sustained and did not drop sharply as observed from particle having lower load of Vi antigen. Thus, along with 'particulate nature' of the polymeric delivery systems, the surface density of antigen also plays an important role in eliciting anti-Vi immune responses. Higher density of antigen on particle surface, promoted effective cross-linking of B-cell receptors and this helped in eliciting enhanced antibody responses. Recently few groups explored the role of surface density of ligands on nanoparticle surface in determining the outcome of immune responses and our results are in line with their findings. Thus apart from size and continuous release of antigen, surface density of antigen on polymer particle play an important role in improving the immunogenicity of Vi polysaccharide.

3.7. Phagocytic Uptake of Fluorescent Labeled Polymer Particles by Macrophages Many of the capsular polysaccharides are known to help the bacteria to evade phagocytosis [55-57]. Vi polysaccharide protects *S. typhi* from the action of anti-0 antibodies and renders it resistant to phagocytosis and complement-mediated killing [48, 55]. Vi polysaccharides have been reported to enhance the survival of *Salmonella typhi* in cultured macrophages [58]. Presence of Vi antigen on the surface of polymeric particles may inhibit the uptake of polymer particles and this may alter subsequent processing and presentation of carrier protein TT. To validate this possibility, phagocytic uptake studies were carried out in murine macrophage cell line J774.A.1.

Figure 10:
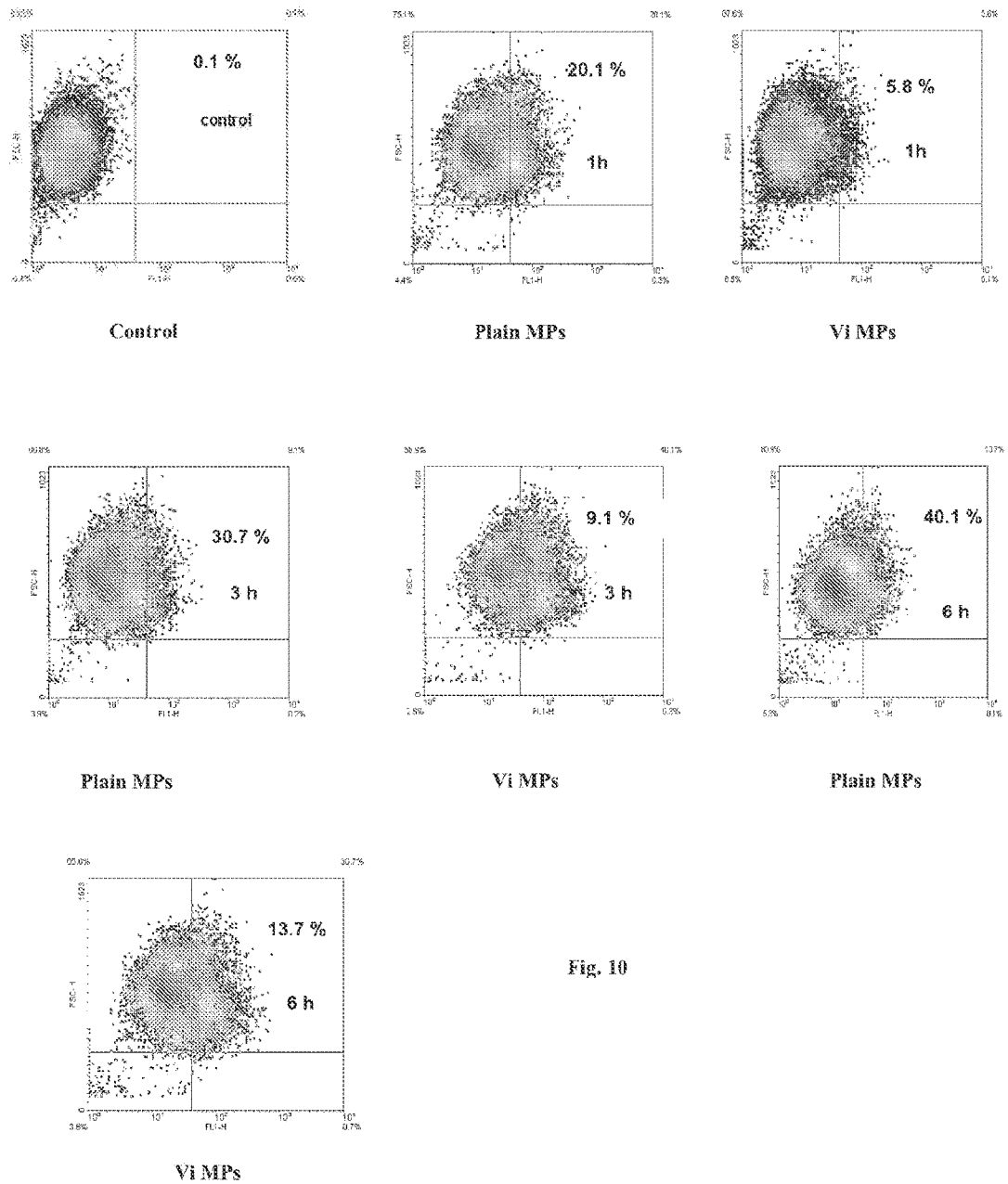
Figure 11:
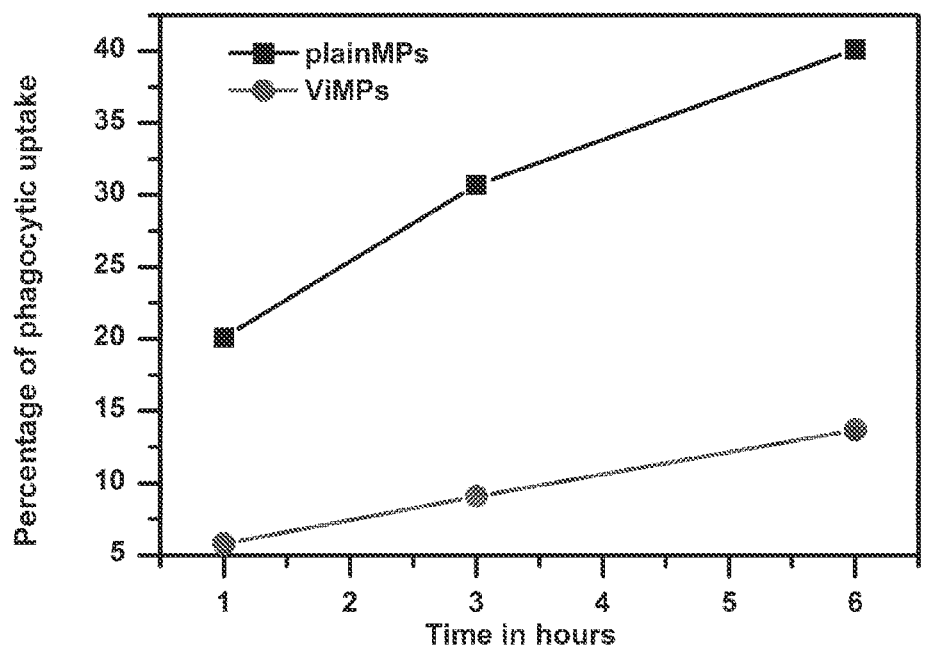
Figure 11:
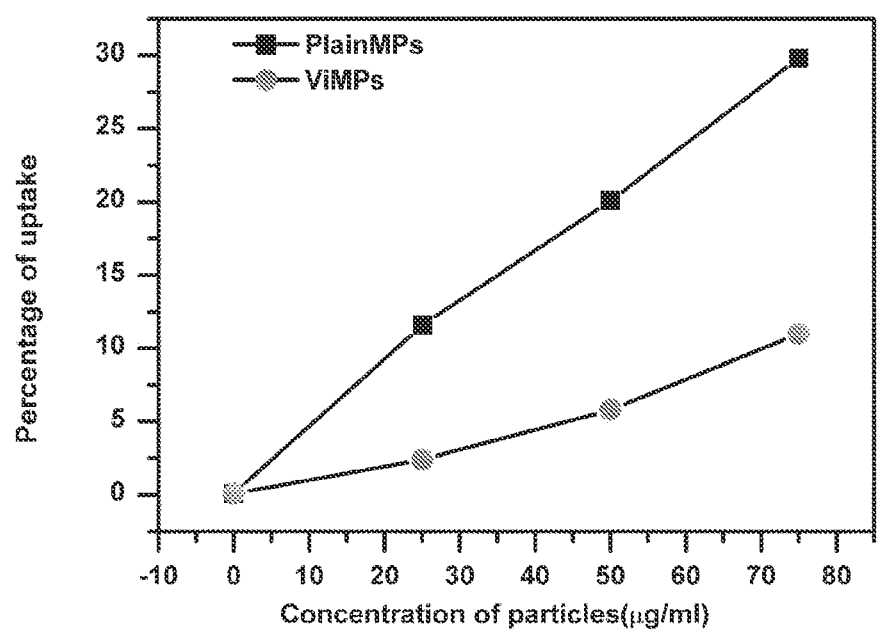

Coumarin labeled particles entrapping Vi antigen and dummy particles were incubated with macrophages and the extent of phagocytosis is analyzed using flowcytometry. Results in FIG. 10 indicated that MPs with Vi antigen on the surface of the particles are phagocytosed less efficiently than plain MPs. The time dependent percentage uptake curve indicated that, at every time point, the uptake of Vi entrapped particle is lower than plain PLA particles (FIG. 11A). This suggested that presence of Vi antigen on the surface of particle inhibited the interaction of polymer particles with APCs. This can affect the processing and presentation of a co-entrapped protein antigen. This explains the lower anti-TT antibody responses from MPs co-encapsulating Vi antigen and TT in the same polymeric matrix. The phagocytic inhibitory effect of Vi polysaccharide is dose dependent and higher concentration of Vi antigen in the particles resulted in higher inhibition of phagocytosis (Fig11B). The dose dependent decrease in uptake of particles entrapping Vi antigen indicated that Vi polysaccharide has anti-phagocytic activities. This anti-phagocytic activity can alter the presentation and processing of entrapped protein antigens.

To further confirm the role of Vi capsular polysaccharide on inhibition of phagocytic uptake, additional studies were carried out after incubating the Vi entrapped particles with anti-Vi antibody (mouse anti-Vi IgG from hybridoma supernatants is a generous gift from Dr. Ayub Qadri, Hybridoma Lab, National Institute of Immunology). Fluorescent tagged Vi entrapped particles as well as plain PLA MPs were pre-incubated with anti-Vi IgG for thirty minutes. After the incubation, particles were centrifuged; the pellets were re-suspended in incomplete media and were added to murine macrophages. After one hour, cells were harvested and analyzed using flow cytometry. The density plots in FIG. 12A suggested that incubation of anti-Vi antibody with Vi entrapped particles, improved its phagocytic uptake. The percentage of polysaccharide entrapped particle uptake is higher than that observed for plain MPs. Pre-incubation of particles with anti-Vi antibody reversed the anti-phagocytic effects of Vi antigen and this helped in improving the phagocytic uptake. This confirms that, Vi polysaccharide inhibits the interaction of Vi entrapped polymer particles with macrophages. Incubating Vi MPs after in vitro release in incomplete DMEM for 6 h also reversed the anti-phagocytic effects of Vi antigen (FIG. 12B). Six hours in vitro release resulted in release of all surface bound Vi antigen and this improved the uptake of Vi MPs. Adding soluble Vi antigen to the culture supernatant did not produce this inhibitory effect. No significant difference in phagocytic uptake of plain MPs is observed in presence of soluble Vi antigen in the culture supernatant (supplementary data S6). This indicated that, the anti-phagocytic effect of Vi antigen is more pronounced when it is present on the particle surface. These observations confirmed that the presence of Vi antigen on the surface of Vi MPs inhibited the phagocytic uptake of these particles. These anti-phagocytic effects interfered with the delivery of entrapped protein antigen to the APCs resulting in less efficient processing and presentation of the antigen. In case of co-entrapped formulations, the Vi antigen interfered with processing and presentation of TT and this resulted in reduced anti-TT antibody responses. Generation of strong anti-TT immune responses is inevitable for recruiting $CD4^+$ T-cell help for Vi polysaccharide. Poor anti-TT immune responses failed to recruit $CD4^+$ T-cell help for Vi antigen and this is reflected in lower anti-Vi antibody responses from co-entrapped formulations. This would be the reason for the lower anti-polysaccharide antibody responses elicited by particle formulations co-entrapping Vi polysaccharide and tetanus toxoid.

3.8. Confocal Microscopic Studies on Phagocytosis of Polymeric Particles by Murine Macrophages Immune responses to polysaccharide antigens were, until recently, assumed to be completely independent of antigen-presenting cells (APCs). It has been reported that a subset of myeloid DCs, termed as plasma blast-associated DCs, supports the differentiation of plasma blasts into antibody-producing plasma cells in response to a soluble TI-2 antigen [59]. In murine studies of pneumococcal infection, APCs were found to be necessary and sufficient to promote survival of polysaccharide antigen-specific B-cells and their differentiation into immunoglobulin M (IgM)-secreting plasma blasts [59]. Considering this, it is of interest to understand how polymeric particles interact with APCs. FIG.13A and FIG.13B illustrate representative confocal laser microscopy images of murine macrophages cells cells phagocytosing polymer particles. It is observed that the particles were within the cell boundary indicating the phagocytosis of polymer particles. This is true for both MPs as well as NPs. The results corroborated the findings from uptake studies, carried out using flow cytometry. It has been well established that late endosomes and lysosomes are the major sites of peptide loading in antigen presenting cells and are collectively called MHCII compartments (MIIC). Since PLA particles are phagocytosed in to membrane bound organelles, it is of interest to analyze whether these particles localize into the lysosomal compartments. Phagocytic uptake studies were carried out in murine macrophages. Lysosomal compartments were labeled with Lysotracker red™ -(red fluorescent dye). Images in FIG. 14A represent the lysosomal clusters of untreated control cells. The images suggested that lysosomal compartments are uniformly distributed throughout the cells. However, in case of cells treated with NPs, the phagocytosed particles co-localized with lysosomal compartments (FIG. 14B) The yellow color resulted from co-localization of red color (lysosomes) and green color (particles) is observed in the image. Moreover, the distributions of lysosomal clusters were also modified and lysosomes were seemed to be preferentially localized only to compartments where particles were present. This indicated that uptake of particles to membrane bound organelle induces remodeling of lysosomal clusters which promoted enrichment of lysosomes, preferentially to the compartments engulfing particles. Same phenomenon is also observed in the case of MPs. The image in FIG.14C represents the enrichment of lysosomal clusters (white arrow, red clusters) into the compartments engulfing particles. Phagocytosis induced preferential enrichment of lysosomes to compartments engulfing particles. This is very important as far as controlled release vaccine formulations are concerned. The preferential enrichment of lysosomes into particle engulfed compartments ensures efficient processing and presentation of antigens from the polymer particles. This could be one of the modes of action of polylactide particles in improving the immunogenicity of entrapped antigens. As shown in FIG.14D, lysosomal remodeling is absent in cells treated with MPs entrapping Vi antigen. Lysosomal clusters were uniformly distributed throughout the cell. The presence of Vi antigen on the surface of the particles abrogated the preferential enrichment of lysosomal clusters into compartments engulfing particles. This indicated that Vi antigen inhibited the localization of lysosomes into the compartments engulfing particles. This has major implications in the case of particulate formulations co-entrapping Vi antigen and proteins. Co-localization of lysosomes and particles in the same compartment is very important for generating immune responses against protein antigens. Vi polysaccharides interfered with processing and there by presentation of tetanus toxoids. Presence of Vi antigen on the surface of polymer particles co-entrapping Vi antigen and TT significantly reduced the phagocytosis as well as lysosomal remodeling effects of polymer particles. This interfered with the processing of released antigens and lowered the anti-TT antibody responses. This explained the failure of formulations co-entrapping polysaccharide and protein antigens to improve the anti-polysaccharide antibody responses.

Observation and Advantages

Polymeric particles based vaccine delivery systems are widely explored to improve the immunogenicity of protein antigens [3, 7, 60]. Numerous reports citing the delivery of various protein antigens are available in the literature and the value of this technology is proven beyond doubt in the case of T dependent protein antigens [3, 4]. The role of particle size, shape, surface morphology and release kinetics in modulating the immune response has been reported extensively [2, 6, 10, 26, 41]. Rapid phagocytic uptake and depot effect of polymeric particles enhances this process [61]. Polymer particles having higher contact surface area promote higher receptor interactions especially for ligands which depend on multivalency for receptor interactions [14, 15]. The magnitude of immune response against T-dependent antigens like proteins depends majorly on the density of peptide-MHC repertoire generated after processing of the protein in endo-lysosomal compartments. But the role of surface ligand density in eliciting the antibody response is also one of the least studied characteristics of these formulations. To delineate this, T-independent antigens would be an ideal model to further validate the importance of polymer particle based delivery system. T-independent antigens which display repeating antigenic determinants on a large polysaccharide back bone elicit antibody responses through B-cell receptor cross linking. Multivalent presentations of antigens promote this receptor cross linking. Contact surface area differences introduced by variations in surface area-volume ratios would reflect on the immune response against these antigens. To validate this concept, in the current study, immunogenicity of polymer particles entrapping Vi polysaccharide is studied in detail. The poor quality of antibody responses to carbohydrates is one of the many obstacles associated with developing carbohydrate-based vaccines [28]. Anti-polysaccharide responses are characterized by lack of immunological memory, isotype switching and affinity maturation and polysaccharide antigens do not elicit antibody responses in neonates and elderly patients [28]. Thus it is of interest to see if these limitations could be solved using polymer particle based vaccination.

Immunization experiments suggested that entrapment of Vi antigens in polymeric particles improved anti-Vi IgG responses. The sustained release of antigen from polymer particles and enhanced B-cell receptor cross linking facilitated by multivalent presentation on particles can be the major contributing factor for this effect. This effect is observed only when polysaccharide antigens were entrapped in polymer particles. Immunization experiments with physical mixture of dummy particles and soluble antigen did not elicit stronger anti-polysaccharide IgG response. This suggested that the particulate nature and sustained release of the antigen from particles played a key role in promoting the antibody response. This is evident from significantly higher memory IgG responses elicited by Vi antigens entrapped in polymer particles. Compared to primary response the secondary antibody response is very high and this is consistent in all particle formulations. The memory antibody response elicited by immunizing $\frac{1}{5}^{th}$ of priming dose of antigen in particle primed group suggested that during boosting, Vi antigen encountered different set of B-cells than the priming stage. These set of B-cells proliferated faster and produced IgG isotypes like IgG1 and IgG2a which are important for opsonophagocytic functions. These observations are very important considering that in general soluble carbohydrate vaccines do not produce memory antibody response and isotype switching. Also rapid recall response elicited by challenge with live *Salmonella typhi* corroborated this finding and support the vaccine delivery potential of polymer entrapped antigens. This indicated that in a real life vaccination scenario, when a live pathogen infects, animal groups immunized with polymer particles entrapped Vi polysaccharide would be able to produce anti-Vi antibodies faster and can help the immune system to clear the pathogen.

A size dependent difference in IgG responses is observed using Vi entrapped polymer particles. Nanoparticle elicited responses comparable to MPs or better memory antibody responses than MPs and this is contrary to the earlier reports with protein antigens. In protein antigens NPs produce significantly low antibody responses than MPs [6, 26]. These differences could be due to the fundamental differences in the interactions of protein (T-dependent) and polysaccharide antigens (T-independent) with the immune system. Unlike protein antigens which need processing and presentation on MHC, polysaccharides in general are neither processed nor presented. T independent antigens cross link the B-cell receptors through multivalent interactions using their repetitive antigenic determinants. Antigens entrapped in polymer particles have the capabilities to promote multivalent interactions of antigen to APCs. Presenting these antigens on a particle can promote the contact surface area for multivalent interactions and enhancements in these interactions were reflected in the higher IgG responses. Compared to MPs, NPs have higher surface area; and this factor would have contributed to the differences in immune responses. The contribution of contact surface area in promoting IgG response is further substantiated by higher IgG responses elicited from polymer particles with higher surface antigen density. Lymphocyte proliferation results where priming with polymer particle formulations induced higher proliferation corroborated the importance of surface interactions. Moreover, phagocytic uptake studies showed that NPs are taken up efficiently by murine macrophages and dendritic cells (data not shown). These antigen presenting cells (APCs) express numerous innate immune receptors like C-type lectins which bind to carbohydrate antigens and promote uptake of carbohydrate antigens to these cells. B-cells interact faster and better to antigens presented on surface of APCs [62]. Higher uptake and subsequent higher delivery of antigens to APCs from NPs would have promoted this process. So along with size, the surface area-volume ratios and surface antigen density of polymer particles are important in promoting the immune response. These observations indicated the importance of above properties of polymer particles while designing delivery systems for different antigens.

Immunization experiments with polymer particles co-entrapping both polysaccharide antigen and carrier protein (tetanus toxoid) in the same matrix did not improve the anti-polysaccharide antibody responses. Though the responses were better than soluble polysaccharide based immunization, it is comparable to immunizations with particles entrapping only polysaccharide. Repeated immunization experiments with particles with different carrier protein-polysaccharide ratios as well as with immunization in animals pre-immunized with carrier protein showed the same effect. Further it is observed that co-entrapment of tetanus toxoid and Vi capsular polysaccharide in same polymer particle suppressed the anti-TT responses. As in the case of glycoconjugate vaccines, generation of effective anti-TT responses is important to drive T-cell help for polysaccharide antigen. Suppression of anti-TT responses by co-entrapment of polysaccharide antigen could be one of the reason for failure of co-entrapped formulations. This suppression effect is further confirmed by phagocytic uptake studies. Inhibition of phagocytic uptake by Vi entrapped polymer particles suggested that presence of Vi and TT in the same polymeric matrix could have affected the processing and presentation of TT. TT being a T-dependent antigen depends heavily on these processes to evoke anti-TT responses. These effects were concentration dependent and specific to Vi polysaccharide. Increasing concentration of Vi entrapped particles in culture media increased the suppression and adding anti-Vi antibodies inhibited the process. Confocal microscopic studies also revealed that presence of Vi on particle surface altered the intracellular fate of MPs. It prevented the localization of particles to endo-lysosomal compartments suggesting the phagocytic inhibitory roles of capsular polysaccharides. Phagocytic inhibitory effects of Vi antigen were more pronounced when Vi antigen is on the surface of a particle. When soluble Vi antigen is added to the culture media this inhibitory effect is very low. Observations from co-entrapped formulations suggest that chemical conjugation of polysaccharide and carrier protein would be essential to promote anti-polysaccharide responses. Though entrapment of polysaccharide antigen alone in polymer particle enhanced the antibody responses, co-entrapment would not be an alternative to glycoconjugates. Plain polymer particle entrapping polysaccharide could serve as an ideal delivery system for these antigens. The results also points to the importance of design principle involved in these delivery systems for presentation of an important class of vaccine components.

CONCLUSIONS

The product is composition of Vi polysaccharide of *Salmonella typhi* entrapped in PLA particle along with excipients. Single dose immunizations of this novel vaccine formulation not only improve the immunogenicity of the carbohydrate antigen but also elicit secondary antibody response upon challenge with soluble Vi polysaccharide. Immunization [of 5 μg] of Vi polysaccharides entrapped PLA particle gave rise to two fold higher antibody titer (IgG) in mice from single dose intramuscular immunization. Memory antibody titers (secondary antibody) in case of animals immunized with polymer particle entrapped Vi polysaccharide were much higher than the primary response. Soluble immunization of Vi polysaccharide did not elicit memory antibody titer. The memory antibody titers observed with polymeric vaccine formulation is sustained at higher level for considerable point of time. The product thus have the capacity to induce immunological memory of carbohydrate antigens with out the use of T cell helper peptide. The vaccine formulation is stable and can be used to immunize children for developing both primary and memory antibody titers.

Multivalent display of polysaccharide antigen on polymer particles provided insights into few important design concepts involved in the formulation and development of these delivery systems. Based on various immunization experiments and in vitro studies the following conclusions are made 1) Polysaccharide antigens entrapped in polymer particles elicit very high anti-polysaccharide antibody responses.

2) Particle based immunizations elicited memory antibody response against the polysaccharide antigen from a single point immunization.

3) Polylactide particle entrapping Vi polysaccharide immunization promoted isotype switching as well as strong recall response on challenge with live *Salmonella typhi*.

4) Unlike in the case of protein antigens nanoparticle based immunizations elicited strong IgG responses.

5) Higher antibody responses were observed with higher surface to volume ratio of particles as well with higher surface antigen density.

6) Vi polysaccharide on the surface of particles showed anti-phagocytic activities.

7) Anti-phagocytic properties reduced the antibody responses against co-entrapped tetanus toxoid and this explains the failure of co-entrapped formulations. These informations can be used to design and develop improved polymer particle based formulation for improving the immunogenicity of T independent antigens.

Acknowledgements

The work is supported both by the core grant of the National Institute of Immunology, New Delhi and project grant (BT/PR4411/PID/06/190/2003) received from the Department of Biotechnology, Government of India. We thank Dr. Ayub Qadri and Dr. Devinder Sehgal, National Institute of Immunology, India for their valuable comments and discussions. We also thank Ms. Rekha Rani and Mr. Ajay for their assistance in Microscopic studies. AKP is partly supported by Tata Innovation Fellowship of DBT, Government of India.

REFERENCES

[1] Cleland J L. Single-administration vaccines: controlled-release technology to mimic repeated immunizations. Trends Biotechnol 1999; 17:25-9.

[2] Jiang W L, Gupta R K, Deshpande M C, Schwendeman S P. Biodegradable poly(lactic-co-glycolic acid) microparticles for injectable delivery of vaccine antigens. Adv Drug Deliver Rev 2005; 57:391-410.

[3] O'Hagan D T, Rappuoli R. Novel approaches to vaccine delivery. Pharm Res 2004; 21:1519-30.

[4] O'Hagan D T, Valiante N M. Recent advances in the discovery and delivery of vaccine adjuvants. Nat Rev Drug Discov 2003; 2:727-35.

[5 Babensee J E. Interaction of dendritic cells with biomaterials. Seminars in immunology 2008; 20:101-8.

[6] Kanchan V, Panda A K. Interactions of antigen-loaded polylactide particles with macrophages and their correlation with the immune response. Biomaterials 2007; 28:5344-57.

[7] Kanchan V, Katare Y K, Panda A K. Memory antibody response from antigen loaded polymer particles and the effect of antigen release kinetics. Biomaterials 2009; 30:4763-76.

[8] Oyewumi M O, Kumar A, Cui Z. Nano-microparticles as immune adjuvants: correlating particle sizes and the resultant immune responses. Expert Rev Vaccines 2010; 9:1095-107.

[9] Yue H, Wei W, Yue Z, Lv P, Wang L, Ma G, et al. Particle size affects the cellular response in macrophages. Eur J Pharm Sci 2010; 41:650-57.

[10] Champion J A, Katare Y K, Mitragotri S. Particle shape: a new design parameter for micro- and nanoscale drug delivery carriers. J Control Release 2007; 121:3-9.

[11] Yoo J-W, Irvine D J, Discher D E, Mitragotri S. Bio-inspired, bioengineered and biomimetic drug delivery carriers. Nat Rev Drug Discov 2011; 10:521-35.

[12] Martinez-Veracoechea F J, Frenkel D. Designing super selectivity in multivalent nano-particle binding. Pro Natl Acad Sci USA 2011; 108:10963-8.

[13] Papp I, Sieben C, Sisson A L, Kostka J, Boettcher C, Ludwig K, et al. Inhibition of influenza virus activity by multivalent glycoarchitectures with matched sizes. Chembiochem 2011; 12:887-95.

[14] Venter P A, Dirksen A, Thomas D, Manchester M, Dawson P E, Schneemann A. Multivalent display of proteins on viral nanoparticles using molecular recognition and chemical ligation strategies. Biomacromolecules 2011; 12:2293-301.

[15] Bondioli L, Costantino L, Ballestrazzi A, Lucchesi D, Boraschi D, Pellati F, et al. PLGA nanoparticles surface decorated with the sialic acid, N-acetylneuraminic acid. Biomaterials 2010; 31:3395-403.

[16] Gupta R K, Goswami D G, Singh R R, Surolia A, Panda A K. Soybean agglutinin coated PLA particles entrapping candidate vaccines induces enhanced primary and sustained secondary antibody response from single point immunization. Eur J Pharm Sci 2012: 45: 282-95.

[17] Steenblock E R, Fadel T, Labowsky M, Pober J S, Fahmy T M. An artificial antigen-presenting cell with paracrine delivery of IL-2 impacts the magnitude and direction of the T cell response. J Biol Chem 2011; 286:34883-92.

[18] Zhou J, Patel T R, Fu M, Bertram J P, Saltzman W M. Octa-functional PLGA nanoparticles for targeted and efficient siRNA delivery to tumors. Biomaterials 2012; 33:583-91.

[19] Szewczyk B, Taylor A Immunochemical properties of Vi antigen from *Salmonella typhi*-Ty2: presence of 2 antigenic determinants. Infect Immun 1980; 29:539-44.

[20] Szewczyk B, Taylor A. Diversity of Vi-related antigens in the microcapsule of *Salmonella typhi*. Infect Immun 1980; 30:661-7.

[21] Lebacq E. Comparative tolerability and immunogenicity of Typherix™ or Typhim Vi™ in healthy adults—0, 12-month and 0, 24-month administration. Biodrugs 2001; 15:5-12.

[22] Tacket C O, Ferreccio C, Robbins J B, Tsai C M, Schulz D, Cadoz M, et al. Safety and immunogenicity of 2 *Salmonella typhi* Vi-capsular polysaccharide vaccines. J Infect Dis 1986; 154:342-5.

[23] Tacket C O, Levine M M, Robbins J B. Persistence of antibody-titers 3 years after vaccination with Vi polysaccharide vaccine against typhoid-fever. Vaccine 1988; 6:307-8.

[24] Keitel W A, Bond N L, Zahradnik J M, Cramton T A, Robbins J B. Clinical and serological responses following primary and booster immunization with *Salmonella typhi* Vi capsular polysaccharide vaccines. Vaccine 1994; 12:195-9.

[25] Mond J J, Vos Q, Lees A, Snapper C M. T-cell independent antigens. Curr Opin Immunol 1995; 7:349-54.

[26] Katare Y K, Muthukumaran T, Panda A K. Influence of particle size, antigen load, dose and additional adjuvant on the immune response from antigen loaded PLA microparticles. International Journal of Pharmaceutics 2005; 301:149-60.

[27] Katare Y K, Panda A K Immunogenicity and lower dose requirement of polymer entrapped tetanus toxoid co-administered with alum. Vaccine 2006; 24:3599-608.

[28] Astronomo R D, Burton D R. Carbohydrate vaccines: developing sweet solutions to sticky situations? Nat Rev Drug Discov 2010; 9:308-24.

[29] Lindberg A A. Glycoprotein conjugate vaccines. Vaccine 1999; 17:S28-S36.

[30] Poolman J, Borrow R. Hyporesponsiveness and its clinical implications after vaccination with polysaccharide or glycoconjugate vaccines. Expert Rev Vaccines 2011; 10:307-22.

[31] Pozsgay V. Synthesis of oligosaccharide-based glycoconjugate vaccines. Glycobiology 2001; 11:933-4.

[32] Farkas P, Bystricky S. Chemical conjugation of biomacromolecules: A mini-review. Chemical Papers 2010; 64:683-95.

[33] Guo Z, Wang Q. Recent development in carbohydrate-based cancer vaccines. Current Opinion in Chemical Biology 2009; 13:608-17.

[34] Hestrin S. The reaction of acetylcholine and other carboxylic acid derivatives with hydroxylamine, and its analytical application. J Biol Chem 1949; 180:249-61.

[35] Yoshida M, Mata J, Babensee J E. Effect of poly(lactic-co-glycolic acid) contact on maturation of murine bone marrow-derived dendritic cells. Journal of Biomedical Materials Research Part A 2007; 80A:7-12.

[36] Katare Y K, Panda A K. Influences of excipients on in vitro release and in vivo performance of tetanus toxoid loaded polymer particles. Eur J Pharm Sci 2006; 28:179-88.

[37] Cordero-Yap L, Rivera R G, Dispo A P, Mallabo J. Evaluation of a new Vi polysaccharide typhoid vaccine in children aged 2-5 years (Reprinted from Journal of Pediatrics, vol 48, pg 85-88, 1999). Biodrugs 2001; 15:27-27.

[38] Szu S C, Li X R, Schneerson R, Vickers J H, Bryla D, Robbins J B. Comparative immunogenicities of Vi polysaccharide-protein conjugates composed of cholera-toxin or its B-subunit as a carrier bound to high-molecular-weight or lower-molecular-weight Vi. Infect Immun 1989; 57:3823-7.

[39] Li X, Sloat B R, Yanasarn N, Cui Z. Relationship between the size of nanoparticles and their adjuvant activity: Data from a study with an improved experimental design. European Journal of Pharmaceutics and Biopharmaceutics 2011; 78:107-16.

[40] Nakaoka R, Inoue Y, Tabata Y, Ikada Y. Size effect on the antibody production induced by biodegradable microspheres containing antigen. Vaccine 1996; 14:1251-6.

[41] Bachmann M F, Jennings G T. Vaccine delivery: a matter of size, geometry, kinetics and molecular patterns. Nat Rev Immunol 2010; 10:787-96.

[42] Dagan R, Poolman J, Siegrist C-A. Glycoconjugate vaccines and immune interference: A review. Vaccine 2010; 28:5513-23.

[43] Poellabauer E M, Petermann R, Ehrlich H J. The influence of carrier protein on the immunogenicity of simultaneously administered conjugate vaccines in infants. Vaccine 2009; 27:1674-9.

[44. Jegerlehner A, Wiesel M, Dietmeier K, Zabel F, Gatto D, Saudan P, et al. Carrier induced epitopic suppression of antibody responses induced by virus-like particles is a dynamic phenomenon caused by carrier-specific antibodies. Vaccine 2010; 28:5503-12.

[45] Peeters C, Tenbergenmeekes A M, Poolman J T, Beurret M, Zegers B J M, Rijkers G T. Effect of carrier priming on immunogenicity of saccharide-protein conjugate vaccines. Infect Immun 1991; 59:3504-10.

[46] Guttormsen H K, Sharpe A H, Chandraker A K, Brigtsen A K, Sayegh M H, Kasper D L. Cognate stimulatory B-cell-T-cell interactions are critical for T-cell help recruited by glycoconjugate vaccines. Infect Immun 1999; 67:6375-84.

[47] Lai Z, Schreiber J R. Antigen processing of glycoconjugate vaccines; the polysaccharide portion of the pneumococcal CRM(197) conjugate vaccine co-localizes with MHC II on the antigen processing cell surface. Vaccine 2009; 27:3137-44.

[48] Garg R, Qadri A. Hemoglobin transforms anti-inflammatory *Salmonella typhi* virulence polysaccharide into a TLR-2 agonist. Journal of Immunology 2010; 184:5980-7.

[49] de Veer M, Kemp J, Chatelier J, Elhay M J, Meeusen E N T. The kinetics of soluble and particulate antigen trafficking in the afferent lymph, and its modulation by aluminum-based adjuvant. Vaccine 2010; 28: 6597-602.

[50] Kemp J M, Kajihara M, Nagahara S, Sano A, Brandon M, Lofthouse S. Continuous antigen delivery from controlled release implants induces significant and anamnestic immune responses. Vaccine 2002; 20:1089-98.

[51] Cui C, Carbis R, An S J, Jang H, Czerkinsky C, Szu S C, et al. Physical and chemical characterization and immunologic properties of *Salmonella enterica* Serovar typhi capsular polysaccharide-diphtheria toxoid conjugates. Clin Vaccine Immunol 2010; 17:73-9.

[52] Fine D P, Kirk J L, Schiffman G, Schweinle J E, Guckian J C. Analysis of humoral and phagocytic defenses against *Streptococcus pneumoniae* serotype-1 and serotype-3. Journal of Laboratory and Clinical Medicine 1988; 112:487-97.

[53 Colino J, Chattopadhyay G, Sen G, Chen Q, Lees A, Canaday D H, et al. Parameters underlying distinct T cell-dependent polysaccharide-specific IgG responses to an intact gram-positive bacterium versus a soluble conjugate vaccine. Journal of Immunology 2009; 183:1551-9.

[54] Bandyopadhyay A, Fine R L, Demento S, Bockenstedt L K, Fahmy T M. The impact of nanoparticle ligand density on dendritic-cell targeted vaccines. Biomaterials 2011; 32:3094-105.

[55] Looney R J, Steigbigel R T. Role of the Vi-antigen of *Salmonella typhi* in resistance to host defense in vitro. Journal of Laboratory and Clinical Medicine 198; 108: 506-16.

[56] Small J M, Mitchell T G. Strain variation in antiphagocytic activity of capsular polysaccharides from *Cryptococcus neoformans* serotype-A. Infect Immun 1989; 57:3751-6.

[57] Dhingra R K, Williams R C J, Reed W P. Effects of pneumococcal mucopeptide and capsular polysaccharides on phagocytosis. Infect Immun 1977; 15: 169-74.

[58] Hirose K, Ezaki T, Miyake M, Li T M, Khan A Q, Kawamura Y, et al. Survival of Vi-capsulated and Vi-deleted *Salmonella typhi* strains in cultured macrophage expressing different levels of CD14 antigen. FEMS Microbiology Letters 1997; 147:259-65.

[59] Garcia De Vinuesa C, Gulbranson-Judge A, Khan M, O'Leary P, Cascalho M, Wabl M, et al. Dendritic cells associated with plasmablast survival. Eur J Immunol 1999; 29:3712-21.

[60] Katare Y K, Panda A K, Lalwani K, Hague I U, Ali M M. Potentiation of immune response from polymer-entrapped antigen: Toward development of single dose tetanus toxoid vaccine. Drug Deliv 2003; 10:231-8.

[61] Trombetta E S, Mellman I. Cell biology of antigen processing in vitro and in vivo. Annu Rev Immunol 2005; 23:975-1028.

[62] Gleeson P A. The sweet side of immunology: glycobiology of the immune system. Immunol Cell Biol 2008; 86:562-3.

We claim:

1. A vaccine composition consisting of a carbohydrate antigen Vi polysaccharide of *Salmonella typhi* entrapped in a polymer particle wherein said polymer particle is selected from poly (DL) lactide (PDLLA) and polylactide-co-glycolide (PLGA), said composition capable of inducing memory antibody response from a single immunization, by multivalent display of polysaccharide antigens on polymeric particles wherein the polymer particles are of a size distribution of 2-8 μm, the composition free of adjuvant.

2. The vaccine composition as claimed in claim 1, wherein said polymer particle is biocompatible and biodegradable.

3. The vaccine composition as claimed in claim 1, wherein said composition in addition to improving the immunogenicity of the carbohydrate antigen, also improves the secondary antibody response upon challenge with soluble Vi polysaccharide.

4. The vaccine composition as claimed in claim 1, wherein said composition from single dose intramuscular immunization gave rise to two fold higher antibody titer (IgG) in mice, induces higher memory antibody titers (secondary antibody) than the primary response in immunized animals or both.

5. A process for preparing a vaccine composition of claim 1 by using w/o/w double emulsion solvent, evaporation method, comprising the steps of
   a. emulsifying internal aqueous phase (IAP) containing Vi antigen, CaCh and Tween 20 into organic phase (OP) 50 mg/ml, PLA solution in dichloromethane by sonication to get the primary emulsion,
   b. adding the primary emulsion (W/O) of step (a) drop wise to external aqueous phase (EAP) containing 2% (w/v) PVP in deionized water,
   c. mixture from step (b) is homogenized for getting micro particles,
   d. the resulting particles from Step (c) is collected by centrifugation (15,000 rpm, 20 min), and
   e. the product of step (d) is lyophilized to obtain free-flowing powder.

6. The process as claimed in claim 5, wherein step (c) homogenization is carried out at 10,000 rpm for 10 min for preparing micro particles.

7. The process as claimed in claim 5, wherein step (d) centrifugation is carried out at 15,000 rpm for 20 minutes.

8. The composition according to claim 1 wherein the antigen load is from 0.366 µg/mg to 7.3 µg/mg.

* * * * *